US008989469B2

(12) United States Patent
Fahimian et al.

(10) Patent No.: US 8,989,469 B2
(45) Date of Patent: Mar. 24, 2015

(54) SYSTEMS AND METHODS FOR SIMULTANEOUS ACQUISITION OF SCATTER AND IMAGE PROJECTION DATA IN COMPUTED TOMOGRAPHY

(75) Inventors: Benjamin Pooya Fahimian, Menlo Park, CA (US); Lei Xing, Palo Alto, CA (US); Bowen Meng, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 288 days.

(21) Appl. No.: 13/332,212

(22) Filed: Dec. 20, 2011

(65) Prior Publication Data

US 2012/0207370 A1    Aug. 16, 2012

Related U.S. Application Data

(60) Provisional application No. 61/459,858, filed on Dec. 20, 2010.

(51) Int. Cl.
*G06K 9/00* (2006.01)
*A61B 6/03* (2006.01)
(Continued)

(52) U.S. Cl.
CPC .............. *A61B 6/032* (2013.01); *A61B 6/4085* (2013.01); *A61B 6/5282* (2013.01); *A61B 6/484* (2013.01);
(Continued)

(58) Field of Classification Search
None
See application file for complete search history.

(56) References Cited

U.S. PATENT DOCUMENTS 5,648,997 A * 7/1997 Chao .......................... 378/98.4
6,618,466 B1    9/2003 Ning
(Continued)

FOREIGN PATENT DOCUMENTS

FR    2864685 A1    7/2005

OTHER PUBLICATIONS

Thilmann et al., Correction of patient positioning errors based on in-line cone beam CTs: clinical implementation and first experiences, May 24, 2006, Radiation Oncology, vol. 1, pp. 16-25.
(Continued)

*Primary Examiner* — Chan Park
*Assistant Examiner* — Iman K Kholdebarin
(74) *Attorney, Agent, or Firm* — Lumen Patent Firm

(57) ABSTRACT

A method of acquiring scatter data and image projection data in computed tomography is provided that includes attenuating a radiation source using a pattern of blockers arranged to provide blocked and unblocked regions of the radiation source, and acquiring image data and scatter data of a target using an imaging device. A scatter map in the projection image can be estimated by interpolation and/or extrapolation of the projection image using an appropriately programmed computer, subtracting the estimated scatter map from the projection image to obtain scatter-corrected projections, reconstructing a CBCT volume using a total variation regularization algorithm, and applying an iterative regularization process to suppress the noise level on the reconstructed CBCT volume. Reconstructing a CBCT volume can include using a total variation regularization algorithm and applying an iterative regularization process to suppress the noise level on the reconstructed CBCT volume, where scatter-induced artifacts are corrected in the projection image.

27 Claims, 21 Drawing Sheets

(51) Int. Cl.
    *A61B 6/00* (2006.01)
    *G06T 11/00* (2006.01)
    *A61N 5/10* (2006.01)

(52) U.S. Cl.
    CPC .............. *G06T 11/005* (2013.01); *G06T 11/006* (2013.01); *A61N 5/1067* (2013.01); *A61B 6/4021* (2013.01); *G06T 2211/421* (2013.01); *A61N 2005/1061* (2013.01)
    USPC .......... 382/131; 382/128; 382/260; 600/567; 600/407; 378/4; 378/20; 378/19; 378/196; 378/22

(56) References Cited

U.S. PATENT DOCUMENTS

| | | | |
|---|---|---|---|
| 6,748,047 B2 | 6/2004 | Gonzalez Trotter et al. | |
| 6,842,502 B2* | 1/2005 | Jaffray et al. | 378/65 |
| 7,046,757 B1* | 5/2006 | Bani-Hashemi et al. | 378/7 |
| 7,308,072 B2 | 12/2007 | Rührnschopf | |
| 7,336,760 B2* | 2/2008 | Virshup et al. | 378/7 |
| 7,463,712 B2* | 12/2008 | Zhu et al. | 378/7 |
| 7,640,607 B2* | 1/2010 | Guertin et al. | 5/601 |
| 7,826,592 B2* | 11/2010 | Jaffray et al. | 378/65 |
| 8,009,794 B2* | 8/2011 | Partain | 378/7 |
| 8,090,074 B2* | 1/2012 | Filiberti et al. | 378/65 |
| 8,144,829 B2* | 3/2012 | Zhu et al. | 378/7 |
| 8,184,767 B2* | 5/2012 | Mishra et al. | 378/7 |
| 8,210,745 B2* | 7/2012 | Yorkston et al. | 378/196 |
| 8,213,694 B2* | 7/2012 | Vaz et al. | 382/128 |
| 8,218,716 B2* | 7/2012 | Handa et al. | 378/4 |
| 8,300,766 B2* | 10/2012 | Handa et al. | 378/65 |
| 8,320,518 B2* | 11/2012 | Partain | 378/7 |
| 8,348,506 B2* | 1/2013 | Yorkston et al. | 378/196 |
| 8,406,373 B2* | 3/2013 | Graham et al. | 378/16 |
| 8,483,363 B2* | 7/2013 | Bertram et al. | 378/157 |
| 8,494,248 B2* | 7/2013 | Souza et al. | 382/132 |
| 8,559,596 B2* | 10/2013 | Thomson et al. | 378/65 |
| 8,611,490 B2* | 12/2013 | Zhang | 378/16 |
| 8,615,118 B2* | 12/2013 | Yi et al. | 382/128 |
| 8,620,052 B2* | 12/2013 | Yang et al. | 382/131 |
| 8,630,473 B2* | 1/2014 | Souza et al. | 382/131 |
| 2006/0088140 A1* | 4/2006 | Fahrig et al. | 378/154 |
| 2007/0014391 A1* | 1/2007 | Mostafavi et al. | 378/63 |
| 2007/0086560 A1 | 4/2007 | Kia et al. | |
| 2007/0268997 A1* | 11/2007 | Zhu et al. | 378/7 |
| 2007/0274435 A1* | 11/2007 | Ning et al. | 378/4 |
| 2007/0280408 A1 | 12/2007 | Zhang | |
| 2008/0025458 A1 | 1/2008 | Virshup et al. | |
| 2008/0080663 A1 | 4/2008 | Haerer | |
| 2009/0067576 A1 | 3/2009 | Maltz | |
| 2009/0171244 A1* | 7/2009 | Ning et al. | 600/567 |
| 2009/0208074 A1* | 8/2009 | Wiersma et al. | 382/128 |
| 2009/0220167 A1* | 9/2009 | Vaz et al. | 382/260 |
| 2009/0225932 A1* | 9/2009 | Zhu et al. | 378/7 |
| 2009/0310835 A1 | 12/2009 | Kaus et al. | |
| 2010/0119033 A1* | 5/2010 | Li et al. | 378/5 |
| 2010/0158335 A1* | 6/2010 | Ning et al. | 382/131 |
| 2010/0278300 A1* | 11/2010 | Yorkston et al. | 378/20 |
| 2010/0318208 A1* | 12/2010 | Schiller et al. | 700/98 |
| 2011/0228901 A1* | 9/2011 | Yorkston et al. | 378/20 |
| 2011/0313231 A1* | 12/2011 | Guertin et al. | 600/1 |
| 2012/0008734 A1* | 1/2012 | Thomson et al. | 378/4 |
| 2012/0008735 A1* | 1/2012 | Maurer et al. | 378/5 |
| 2012/0019512 A1* | 1/2012 | Yang et al. | 345/419 |
| 2012/0207370 A1* | 8/2012 | Fahimian et al. | 382/131 |
| 2012/0236982 A1* | 9/2012 | Star-Lack et al. | 378/7 |
| 2012/0263360 A1* | 10/2012 | Zhu et al. | 382/131 |
| 2012/0294424 A1* | 11/2012 | Chin et al. | 378/65 |
| 2013/0004041 A1* | 1/2013 | Yang et al. | 382/131 |
| 2013/0004042 A1* | 1/2013 | Yang et al. | 382/131 |
| 2013/0010927 A1* | 1/2013 | Seppi et al. | 378/86 |
| 2013/0051516 A1* | 2/2013 | Yang et al. | 378/4 |
| 2013/0051519 A1* | 2/2013 | Yang et al. | 378/19 |
| 2013/0070991 A1* | 3/2013 | Yang et al. | 382/131 |
| 2013/0077741 A1* | 3/2013 | Yorkston et al. | 378/20 |
| 2013/0188848 A1* | 7/2013 | Helm et al. | 382/131 |
| 2013/0294572 A1* | 11/2013 | Jaffray et al. | 378/7 |
| 2014/0037044 A1* | 2/2014 | Ning et al. | 378/4 |

OTHER PUBLICATIONS

Siewerdsen et al., A simple, direct method for scatter estimation and correction in digital radiography and cone-beam CT, 2006, Medical Physics, vol. 31, No. 1, pp. 187-197.

* cited by examiner (a)  (b)

(a)

(b)

(c)

(a)        (b)

(a)

(b)

(a)

(b)

(c)

(a)

(b)

SYSTEMS AND METHODS FOR SIMULTANEOUS ACQUISITION OF SCATTER AND IMAGE PROJECTION DATA IN COMPUTED TOMOGRAPHY

CROSS-REFERENCE TO RELATED APPLICATIONS

This application claims priority from U.S. Provisional Patent Application 61/459,858 filed Dec. 20, 2010, which is incorporated herein by reference.

STATEMENT OF GOVERNMENT SPONSORED SUPPORT

This invention was made with Government support under contract 0854492 awarded by National Science Foundation. The Government has certain rights in this invention.

FIELD OF THE INVENTION

The present invention relates generally to Computed Tomography (CT). More particularly, the invention relates to relate to novel systems and methods for simultaneously acquiring scatter and image projection data in CT imaging modalities.

BACKGROUND OF THE INVENTION

The presence of scatter in projectional images acquired for tomographic reconstruction is currently a critical limiting factor in transmission CT modalities, such as medical x-ray Cone-Beam CT (CBCT), as it results in a significant degradation of the tomographic image quality and accuracy. In the field, the prominent methods that have been proposed so far for scatter correction include Monte Carlo methods, which are accurate but slow, analytical methods, which may lack the complexity to deal with heterogeneous objects (such as patients) accurately, and scatter suppression methods (such as the use of anti-scatter grids or the air gap method), the efficacy of which thus far have been limited. More recently, a proposed method included an experimental blocker method for cases where there exists repeat scans, such as in image guidance in radiotherapy, an initial partially blocked scan can be used to experimentally determine the patient specific scatter profile, and then through a process such as rigidly registration, subsequent scans can be corrected using the stored scatter profiles. Although this method has yielded promising results, it is specific to cases where there exists repeat scans, requires registration, and relies on the assumption that the patient configuration, such as positioning and weight, has not changed during the course of treatment.

Further, the x-ray scatter incurred to detector represents a bottleneck problem in volumetric image guided and adaptive radiation therapy. Several methods using a beam blocker for the estimation and subtraction of scatter have been proposed. However, due to missing information obstructed by the blocker, such methods require dual scanning or dynamically moving blocker to obtain a complete volumetric image.

CBCT systems mounted on the gantry of the linear accelerator have become an integral method for volumetric image guidance in modern radiotherapy. However, due to the broad beam geometry utilized in such systems, projection data are significantly convoluted by x-ray scatter, which in turn degrades the quality of CBCT, leading to a decrease in contrast, shading artifacts, and inaccuracies of CT number. Consequently, the utility of CBCT scans in important applications, such as adaptive radiotherapy, is limited. An efficient and practical scatter-corrected reconstruction technique is thus necessitated to maximize the usefulness of the on-board CBCT imaging system.

Many scatter correction strategies have been proposed in literature with recent research focused on beam blocker-based techniques. In these beam blocker-based approaches, the detected information in blocked regions is attributed to the scatter and scatter-free primary data are obtained by subtracting the estimated scatter data in blocked regions from the image data in unblocked regions. These methods can be divided into two major parts: a single scanning and a dual scanning. In the single scanning scheme, the missing information blocked by the lead strips is made available through interpolation. This interpolation may lead to the degradation of CBCT image quality due to unphysical smoothing and loss of geometric fidelity, especially in regions with sharp boundaries or edges. To get reasonable sampling rate in a single-rotation, a dynamically moving blocker-based approach has been introduced, but such a method necessitates an accurate synchronization between a finely motor-controlled blocker and a gantry rotation to avoid lag effects in the acquisition process. The dual scanning scheme has been attempted to avoid missing information caused by the beam blocker. A prior image based approach is to measure the scatter distribution with partially-blocked projection data taken at the initial day of treatment using a blocker. The estimated scatter distribution is used to correct later CBCT scans of the same patient. Though, this approach needs a minimal amount of extra imaging dose to generate a prior image, its accuracy depends on an image registration technique to correct geometric inaccuracy between prior and subsequent images because there are mismatched patient setup and intra-fractional organ variations. Another approach is to stitch up two projections with non-overlapped regions for complete projections by a dual-rotation CBCT scans. However, additional imaging dose and mechanical modifications of the current system are inevitable.

What is needed is a method of detecting CBCT source scatter data simultaneously with image projection data in a single scan, and correcting for scatter-induced artifacts in the CBCT image.

SUMMARY OF THE INVENTION

To address the needs in the art, a method of acquiring scatter data and image projection data in computed tomography is provided that, according to one embodiment, includes attenuating a radiation source using a pattern of blockers, where the blockers are arranged to provide blocked and unblocked regions of the radiation source, and acquiring image data and scatter data of a target using an imaging device.

In one aspect of the current embodiment, a relative blocker motion is introduced during the image data acquisition and the scatter data acquisition. Here, in one aspect, the relative blocker motion can include moving blockers and a stationary target, a moving target and stationary blockers, the moving blockers and the moving target, rotating the target about a target axis, where the target axis is parallel to an axis of symmetry of the target pattern. In another aspect, the relative motion includes moving a focal point of the radiation source relative to the blocker position or moving a position of the radiation source relative to the blocker position.

According to another aspect of the current embodiment, the blocker comprises lead.

In a further aspect of the current embodiment, the pattern of blockers can include horizontal strips, vertical strips, diagonal strips, checker board, asymmetric horizontal strips, or asymmetric vertical strips.

In another aspect of the current embodiment, the pattern of blockers are arranged according to a thickness of each the blocker.

According to one aspect of the current embodiment, the scatter data is acquired at an acquisition frequency that is lower that an acquisition frequency of the image data.

In another embodiment, a method of correcting scatter-induced artifacts in cone-beam computed tomography (CBCT) is provided that includes disposing blockers between an imaging source and a patient and disposing the patient between the blocker and a detector, where the detector includes a region of reconstruction (ROR), where the blockers block the boundaries of the ROR, acquiring CBCT projection data on the ROR while rotating the imaging source, the blocker and the detector about an axis of the patient, where the projection data includes primary signal data and scatter signal data, where the scatter signal data includes a model of a convolution of the primary signal data with a kernel function, where the convolution kernel function estimates the scatter signal data from the primary signal data and, correcting the CBCT projection data for the scatter signal data in the ROR by extracting a boundary scatter map from the ROR, initially estimating the boundary scatter signal data in the ROR using interpolation of the boundary scatter data, calculating the kernel function by applying a least squared minimization to a log transformed scatter and using projection of the ROR, where the kernel function includes an overall magnitude adjustment and a local adjustment from the projection, estimating a scatter map by reconstructing a complete scatter distribution for each the projection using a constrained optimization (CO) and compressed sensing (CS), subtracting the scatter map from the projection signal data using a threshold method, and using a Feldkamp-Davis-Kress (FDK) algorithm to reconstruct a scatter free image.

According to one aspect of the current embodiment, the projection image acquisition includes using asymmetric half beam blockers.

In a further aspect of the current embodiment, the total variation regularization algorithm includes a total variation regularized Feldkamp-Davis-Kress (FDK) algorithm based on a cosine weighting function.

In yet another aspect of the current embodiment, the variation regularization algorithm is applied according to a minimization using a steepest gradient decent optimization method.

According to another aspect of the current embodiment, the scatter and image data are obtained simultaneously.

In a further aspect of the current embodiment, the projection image includes using a half beam blocker, where the half beam blocker includes unblocked regions on a first half side of a projection region and partially blocked regions on a second half side of the projection region.

According to a further aspect of the current embodiment, the corrected scatter-induced artifacts in the projection image are accomplished from a single-rotation CBCT scan.

In one aspect of the current embodiment, the interpolation and/or extrapolation of the projection image comprises a 1D cubic B-Spline interpolation/extrapolation applied to the projection imaged, where patient specific scatter information is derived by using scatter distributions on blocker strips.

According to another aspect of the current embodiment, the blocker comprises lead.

In another aspect of the current embodiment, the blockers are arranged in a pattern, wherein the pattern of blockers can include horizontal strips, vertical strips, diagonal strips, checker board, asymmetric horizontal strips, or asymmetric vertical strips.

In a further aspect of the current embodiment, the blockers are moved actively during the projection image acquisition, where the blocker motion can include moving blockers relative to a stationary target, a moving target relative to stationary blockers, the moving blockers and the moving target, or rotating the target about a target axis, wherein the target axis is parallel to an axis of symmetry of the target pattern.

In yet another aspect of the current embodiment, the blockers are arranged in a pattern, where the pattern of blockers are arranged according to a thickness of each the blocker.

In yet another aspect of the current embodiment the blockers are moved actively during the projection image acquisition, wherein the blocker motion includes moving a focal point of the radiation source relative to the blocker position or moving a position of the radiation source relative to the blocker position.

In yet another aspect of the current embodiment, the scatter data is acquired at an acquisition frequency that is lower that an acquisition frequency of the image data.

In a further embodiment of the invention, a method of correcting scatter-induced artifacts in cone-beam computed tomography (CBCT) is provided that includes disposing blockers between an imaging source and a patient and disposing the patient between the blocker and a detector having a region of reconstruction (ROR), where the blockers block the boundaries of said ROR, acquiring CBCT projection data on the ROR while rotating the imaging source, the blocker and the detector about an axis of said patient, where the projection data includes primary signal data and scatter signal data, where the scatter signal data includes a convolution of the primary signal data with a kernel function, where the convolution kernel function estimates the scatter signal data from the primary signal data, and correcting the CBCT projection data for the scatter signal data in the ROR that includes extracting a boundary scatter map from said ROR, initially estimating said boundary scatter signal data in said ROR using interpolation of said boundary scatter data, determining an overall magnitude adjustment and a local adjustment of said bilinear interpolated scatter using a least squares minimization, estimating a scatter map by reconstructing a complete scatter distribution for each said projection using a constraint optimization (CO) and a compressed sensing (CS), subtracting said scatter map from said projection signal data, and using a half-fan or full-fan tomographic reconstruction algorithm wherein said half-fan or full-fan tomographic reconstruction algorithm comprises a Feldkamp-Davis-Kress (FDK) algorithm or regularized iterative reconstruction algorithm, to reconstruct a scatter free image.

According to one aspect of the current embodiment, the projection image acquisition includes using asymmetric half beam blockers.

In another aspect of the current embodiment, the total variation regularization algorithm includes a total variation regularized Feldkamp-Davis-Kress (FDK) algorithm based on a cosine weighting function.

According to one aspect of the current embodiment, the variation regularization algorithm is applied according to a minimization using a steepest gradient decent optimization method.

In a further aspect of the current embodiment, the scatter and image data are obtained simultaneously.

According to yet another aspect of the current embodiment, the projection image comprises using a half beam blocker, where the half beam blocker includes unblocked regions on a first half side of a projection region and partially blocked regions on a second half side of the projection region.

In a further aspect of the current embodiment, the corrected scatter-induced artifacts in the projection image are accomplished from a single-rotation CBCT scan.

In one aspect of the current embodiment, the interpolation and/or extrapolation of the projection image comprises a 1D cubic B-Spline interpolation/extrapolation applied to the projection imaged, where patient specific scatter information is derived by using scatter distributions on blocker strips.

In another aspect of the current embodiment, the blocker comprises lead.

In a further aspect of the current embodiment, the blockers are arranged in a pattern, wherein the pattern of blockers can include horizontal strips, vertical strips, diagonal strips, checkerboard, asymmetric horizontal strips, or asymmetric vertical strips.

In yet another aspect of the current embodiment, the blockers are moved actively during the projection image acquisition, where the blocker motion can include moving blockers relative to a stationary target, a moving target relative to stationary blockers, the moving blockers and the moving target, or rotating the target about a target axis, where the target axis is parallel to an axis of symmetry of the target pattern.

According to a further aspect of the current embodiment, the blockers are arranged in a pattern, where the pattern of blockers are arranged according to a thickness of each the blocker.

In yet another aspect of the current embodiment, the blockers are moved actively during the projection image acquisition, where the blocker motion comprises moving a focal point of the radiation source relative to the blocker position or moving a position of the radiation source relative to the blocker position.

In a further aspect of the current embodiment, the scatter data is acquired at an acquisition frequency that is lower that an acquisition frequency of the image data.

According to another embodiment of the invention, a method of producing an imaging modality for reconstructing and displaying the cross-sectional scatter signal throughout an imaging subject is provided that includes using a CT machine to subtract uncorrected CT reconstruction slices comprising a combination of a scatter signal and a primary signal from corresponding scatter corrected CT slices to output a cross-sectional image of the scatter-distribution across an imaging subject volume specific.

In another embodiment of the invention, a method of producing scatter-corrected CT images and displaying a cross-sectional scatter signal throughout an imaging subject is provided that includes inducing a scatter signal in a CT image using a blocker, using a CT imaging machine to subtract uncorrected CT reconstruction slices comprising a combination of a scatter signal and a primary signal from a corresponding scatter corrected CT slice to output at a cross-sectional scatter-distribution across a limited number of the slices, using the CT imaging machine to interpolate, extrapolate, and or compress sensing data on the number of limited the slices of a first partial target volume to output at a cross-sectional scatter distribution approximated by other the slices throughout a remaining partial target volume, where the cross-sectional scatter distribution is used to approximate a three-dimensional cross-sectional distribution of the scatter, subtracting the approximated three-dimensional cross-sectional distribution of scatter from an uncorrected cross-sectional CT reconstruction, where the uncorrected cross-sectional CT reconstruction comprises said primary signal and said scatter signal, to output a scatter corrected CT reconstruction image.

DETAILED DESCRIPTION

Figure 1:
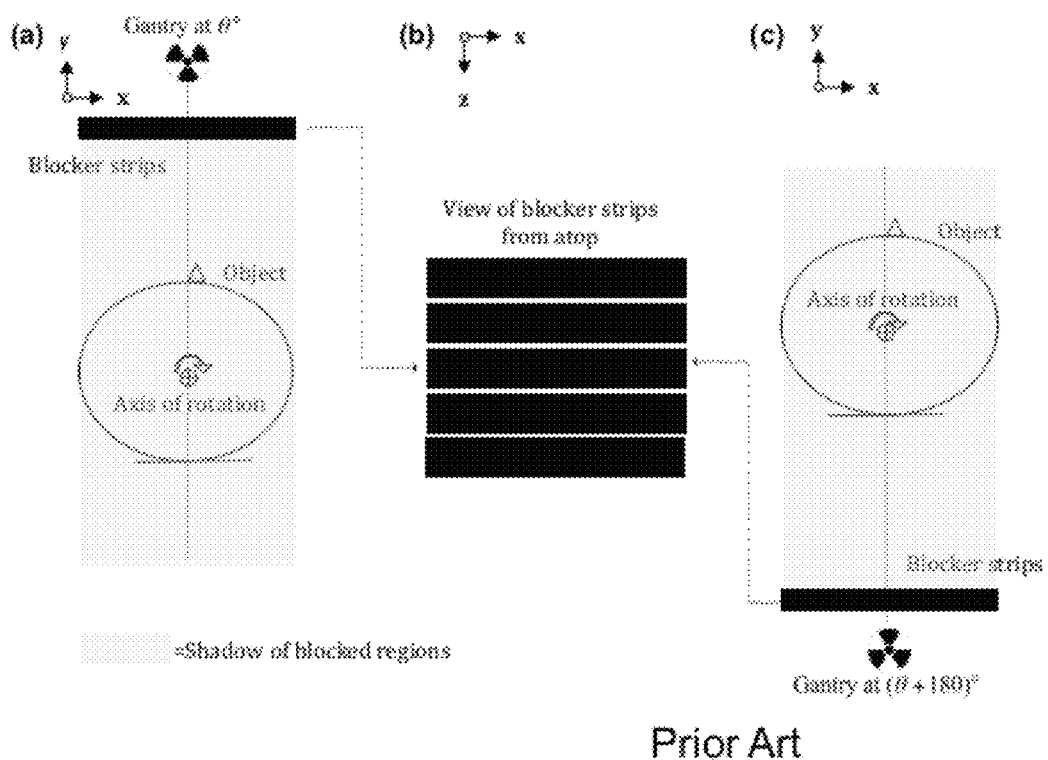
FIGS. 1a-1c show prior art schematic drawings of the geometry of a previous blocker scheme.

The current invention provides methods through which the scatter signal can be experimentally detected simultaneously while the projectional data is being acquired subsequently, where the detected scatter data can be used for scatter correction in the reconstruction. One embodiment of the invention provides a practical method to significantly improve tomographic imaging quality through the removal of scatter artifacts resulting in considerably increased contrast, fidelity, and CT number accuracy in tomographic reconstructions. The invention provides advancement to the field of medical x-ray CT in which CBCT systems, widely utilized for image guidance in radiotherapy, lack a practical method for accounting for scatter. Additionally, the invention is applicable to a multitude of tomographic imaging modalities such as diagnostic circular and helical CBCT, microCT, megavoltage CT, as well as tomographic imaging modalities utilizing a variety of different radiative sources and geometries (such as Transmission Electron Microscopy, Synchrotron Tomography, Proton CT, etc.).

In one aspect, the invention provides scatter correction in a multitude of computed tomographic imaging modalities in the medical, biological, and physical fields. Some advantages of the invention include patient/object-specific scatter correction, concurrent detection of tomographic image data and scatter data, yielding an accurate and adaptive method for scatter correction in tomographic reconstruction, and elimination of scatter artifacts resulting in higher contrast, image quality, and CT number accuracy.

Many variations of the current invention are presented. Such variations include many different blocker pattern designs and motions that utilize the invention, where the blockers can include multiple disconnected regions. For example, the number, shape, thickness, spacing, composition and pattern of the proposed blocker strips can all be varied as desired by the user while still utilizing the different embodiments of the invention. Some exemplary features include various blocker designs, profiles and patterns for scatter correction. Different blocker motions for scatter correction, and acquisition of patient specific image projection data and scatter data in a concurrent and extensive manner that makes accurate tomographic reconstruction possible.

The current invention provides a method where the use of multidetector computed tomography (MDCT) is eliminated by either moving the blocks, or providing special rotationally assymetric patterns, where the invention both acquires the scatter data, and a new corrected and complete CBCT based on that acquisition. In the current invention, a method is provided on how the full image data can be reconstructed from solely blocked CBCT by introducing motion or special geometric patterns.

The invention includes methods and systems that generalize a blocker method in such a manner that scatter profiles can be simultaneously acquired during the process of acquiring tomographic projection data, where patient specific scatter profiles are detected in the same scanning procedure used for acquiring patient projection data. This allows for concurrent scatter correction and image reconstruction that does not rely on repeat scans, registration, or assumptions on the patient configuration, in a manner that is general and practical, resulting in accurate patient specific scatter correction reconstruction.

According to the invention, it is assumed that the blocker is an attenuating material appropriate for radiation source, which reduces the incident radiation by some factor. For x-rays, such a material may be lead or another high Z composite. It is understood that the attenuating material and thickness will be different for different sources (i.e., electrons, protons) and will be determined through preference of the user.

It is noted that no assumption on the particular reconstruction algorithm is made for the systems disclosed as they represent general acquisition methods. The use of the acquisition methods with various analytic, iterative, regularized, and compressed sensing reconstructions are understood.

It is further understood that many variations can be deduced from the general ideas presented in the disclosure. Such variations include many different blocker pattern designs and motions that utilize the same ideas of the invention. For example, the number, shape, thickness of each individual strip (e.g., FIG. 3e), dimensions of each individual strip, spacing, composition and pattern of the proposed blocker strips can all be varied as desired by the user while still utilizing the invention.

As an example of the benefits gained by the invention, in a prior art transaxial design, blocking strips are disposed parallel to the transaxial direction, i.e. perpendicular to the axis of rotation, as shown in FIGS. 1a-1c. As a result of such, for a given circular scan, the strips continually block the same group of axial slices at different gantry angles, leading to fully missing data across corresponding slices, which is inadequate for image reconstruction. To alleviate this issue, the current invention provides blocks that are not aligned transaxial, but instead, aligned axially in an asymmetric fashion, so that as the gantry is rotated, the portions of the object blocked at a given angle, are unblocked at different gantry angles. This is schematically demonstrated for one embodiment of the invention in FIGS. 2a-2c. It is noted that the triangle on the imaging object is blocked off in FIG. 2a at angle θ°, while at (θ+180)° in FIG. 2c, the triangle is no longer blocked. Using this setup and for example a 360° acquisition, the opposing views can be used to fill in the block and unblocked regions of the respective opposing views, resulting in both image projection data (unblocked regions), and scatter detections (blocked regions), that can be utilized by any desired reconstruction algorithm. Unlike the previous work where some slices in the z directions were always fully blocked off, here, to a major extent, both image and scatter data will exist for all slices.

Figure 2:
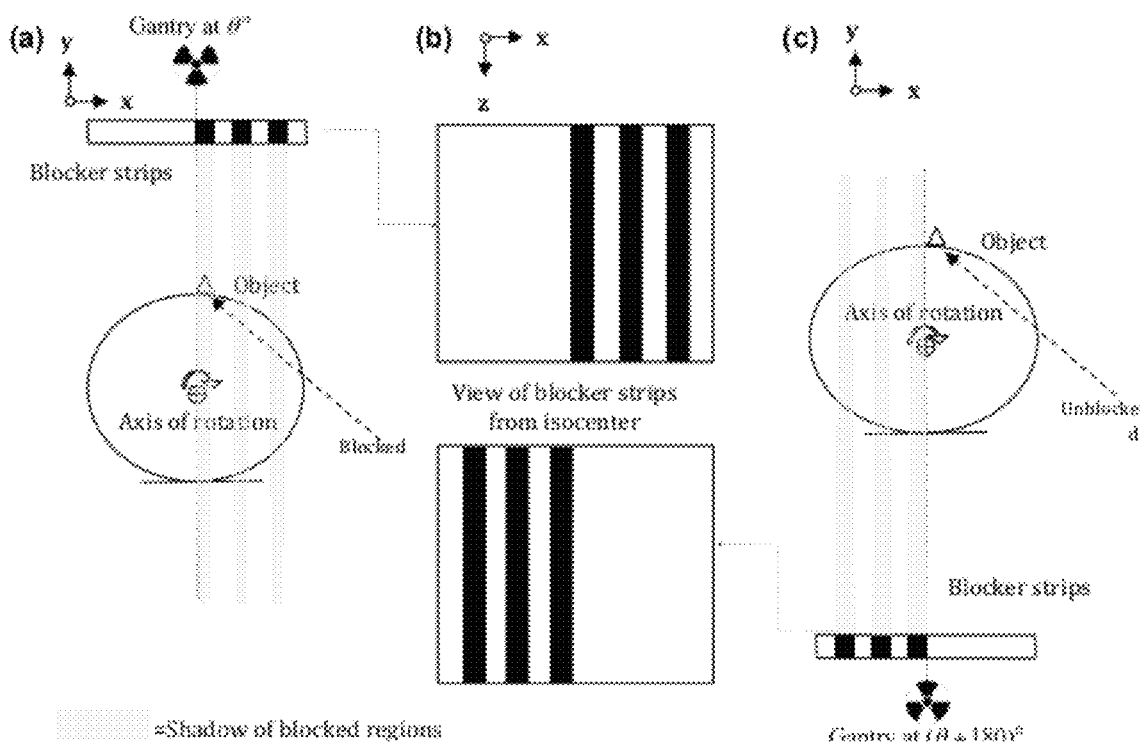
FIGS. 2a-2c show transaxial strips that are perpendicular to the axial direction, according to one embodiment of the invention.

It is noted that FIGS. 2a-2c provide one embodiment of the invention to use axial patterns that are centrally asymmetric.

According to another embodiment, the invention includes axial strips that are symmetric about the x-axis. Such configurations can be used on their own to yield partial scatter and image projection data.

A center of rotation or center of detector offset can be utilized with the above-mentioned configurations. As in a quarter detector offset in tomographic acquisition, such an offset can cause the configurations to become asymmetric with rotation of the gantry, which may be of use (especially if the strip pattern is symmetric) in interleaving blocked and unblocked embodiments.

This method, shown in FIGS. 2a-2c has been fully implemented experimentally on a LINAC based on-board imager, in which the scatter is approximated by the blocked region of the opposite view, while the image is reconstructed with a half-fan algorithm of the unblocked regions after the subtraction of the scatter approximate.

Figure 3:
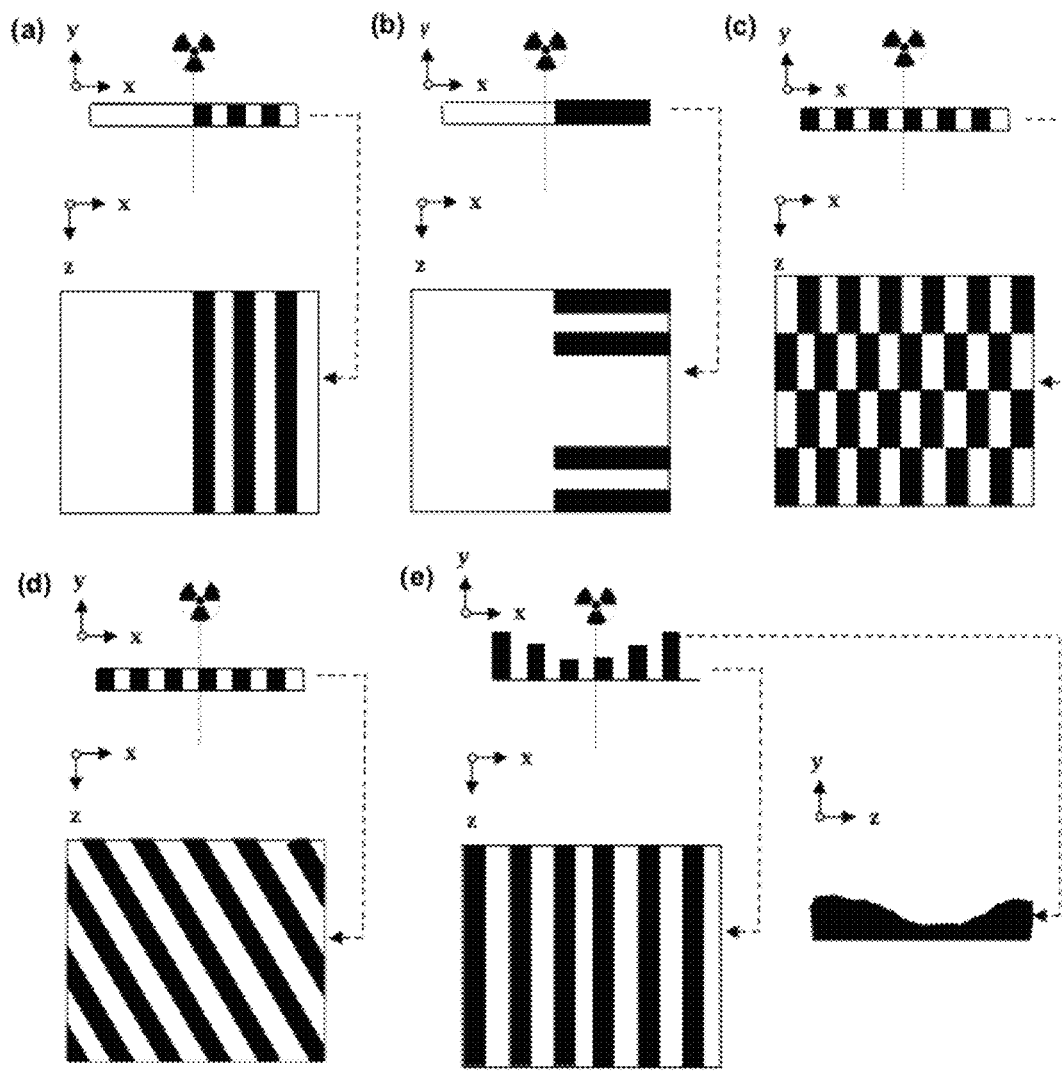
FIGS. 3a-3e show various geometries of different embodiments of the current invention.

FIGS. 3a-3e give variations of the current invention. It is noted that the blocks can be horizontal as in FIG. 3b and FIG. 3d or of differing designs, but all of which utilize the same underlying foundation outlined. As an example, in the embodiment in FIG. 3d, given full 360 degree rotation, reconstruction of the volume can be divided in two half-fan reconstructions of the left and right regions, with the scatter subtracted correspondingly from the data underneath the left and right region, respectively. As the left and right region asymmetrically block different portions of the anatomy, the reconstructed images of the unblocked regions of the two corrected half-fan reconstructions can be interleaved to yield combined set of corrected reconstructions slices that cover the entire volume.

The one aspect of this portion of the invention is to acquire a more extensive set of image projection and scatter detection data by introducing relative blocker motion while the projections are being acquired, using one or combination of methods described below during the scanning procedure.

Figure 4:
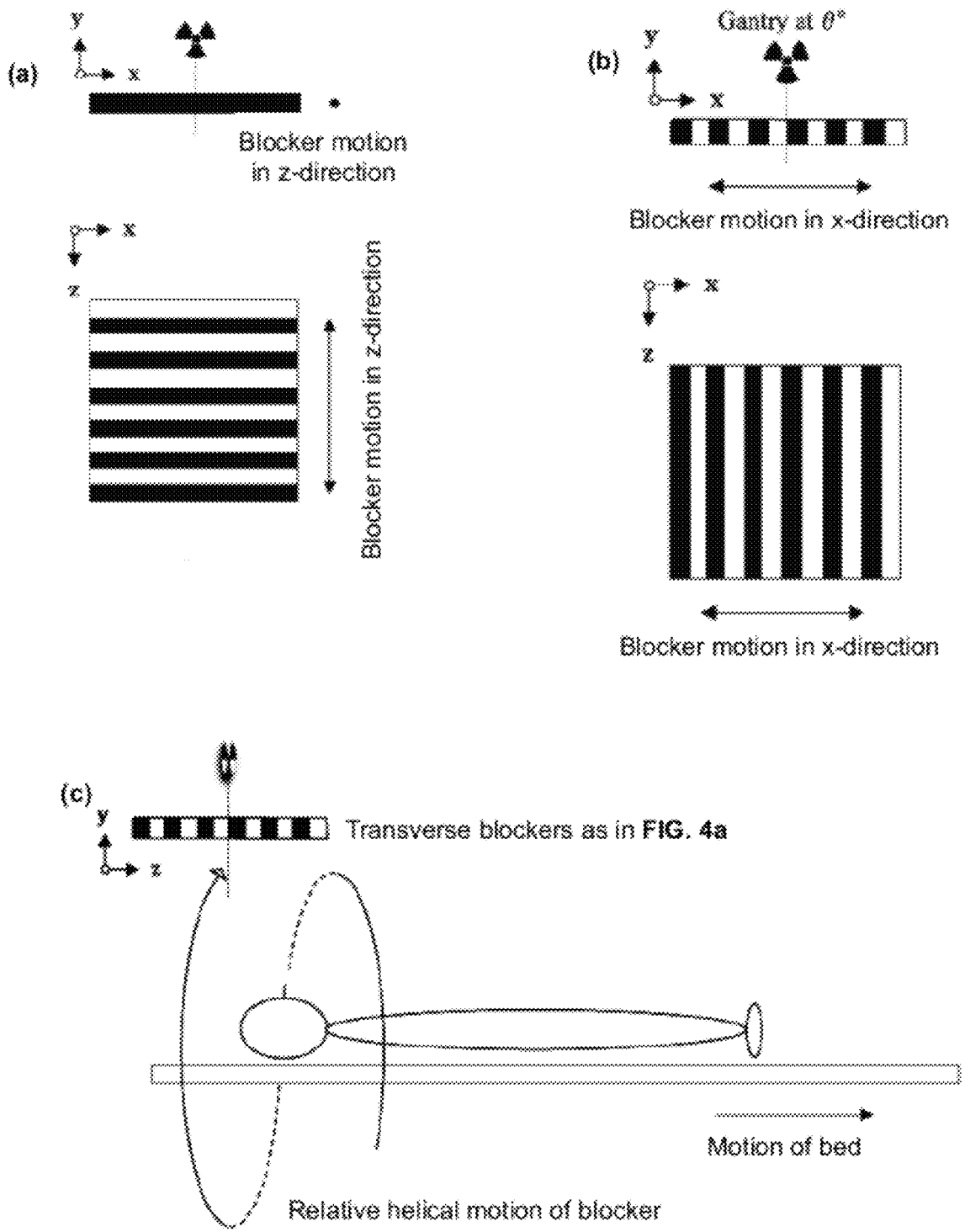
FIGS. 4a-4c show schematic demonstrations for motion of a transverse and an axial blocker pattern, respectively, according to embodiments of the current invention.

According to one embodiment of the invention, a moving blocker method includes a blocker panel in front of the source that is moved during the acquisition as the gantry is in motion (or for biological applications, the object is being rotated). The motion of the blocker relative to the source may be periodic, non periodic, unidirectional (e.g., for a long blocker), or can occur discretely at certain angles (e.g., every user defined degrees during the scan). In addition, there is no restriction place in the invention that the motion must necessarily be coplanar. As the blocker is moved during the acquisition, it results in different regions of the object being exposed to the open and blocked regions. By means of example and not exclusion, FIG. 4a-4c schematically demonstrate such a motion for a transverse and axial blocker pattern, respectively. As the blocker in say FIG. 4a is moved, slices in the z-direction that were once blocked will become unblocked and projection data for image reconstruction can be detected; similarly, detection of scatter profiles in slices that were once unblocked can be made as the blocker moves over the corresponding slice. The detections can then be interleaved to result in a more extensive projection and scatter data set relative to acquisitions where the blocker is in a static location relative to the source.

According to another aspect, the invention can include a moving and changing blocker/collimator embodiment, where similar to multi-leaf collimators (MLC) used radiotherapy, an MLC device, or an MLC-like device is placed in front of the source through which the blocking pattern can be changed in an automated manner. It is understood that in such a method the MLC shape-change can occur dynamically as the gantry is rotated, but also multiple changes of blocker design at any given gantry angle can occur. Using such a device, all the patterns presented in this discussion using static blockers can be produced, as well as new dynamic patterns. Such a method can be implemented with existing technology, for example by using the MLC on clinical linear accelerators; this is particularly applicable in megavoltage CT imaging in which currently an open MLC is used, but can instead be modified so the MLC blocking shape changes during the megavoltage CT acquisition. Following such an acquisition, the aggregate data from the different blocked (i.e., scatter detection regions) and unblocked regions (i.e., image data regions) can be used for scatter correction and image reconstruction.

According to one embodiment, a relative motion induced by movement of couch (i.e., imaging object position) is provided. In one embodiment a sequential movement of the couch is provided, where, instead of moving the blocker relative to the source, the couch position is transversed one or multiple times. For example a full or partial scan may acquired with a specific blocker, such as the transverse one in FIG. 4a, followed by an appropriate movement of the couch (by for example the a shift in the z-direction approximately equal to the shadow of a given block), followed by another scan. The data from this partial or full scans can be combined to result in a more extensive coverage of projection data and scatter data that can be more accurately reconstructed.

In another embodiment, continuous movement of the couch (e.g., helical scans) is provided, where the couch is holding the imaging object and is continuously moved in or out while the gantry rotates, resulting in a relative helical path. Such a path is similar to what is utilized in diagnostic CT scans. Here, the inclusion of the blocker in conjunction with helical motion allows for detection of more extensive projection and scatter data as the blocker is in relative motion in the z (slice direction). The helix can be of different pitches corresponding to different desired sampling. One exemplary application of this embodiment is for scatter correction in emerging diagnostic kilovoltage scanners in which a large number of slices are illuminated, i.e. cone-beam geometry.

Figure 5:
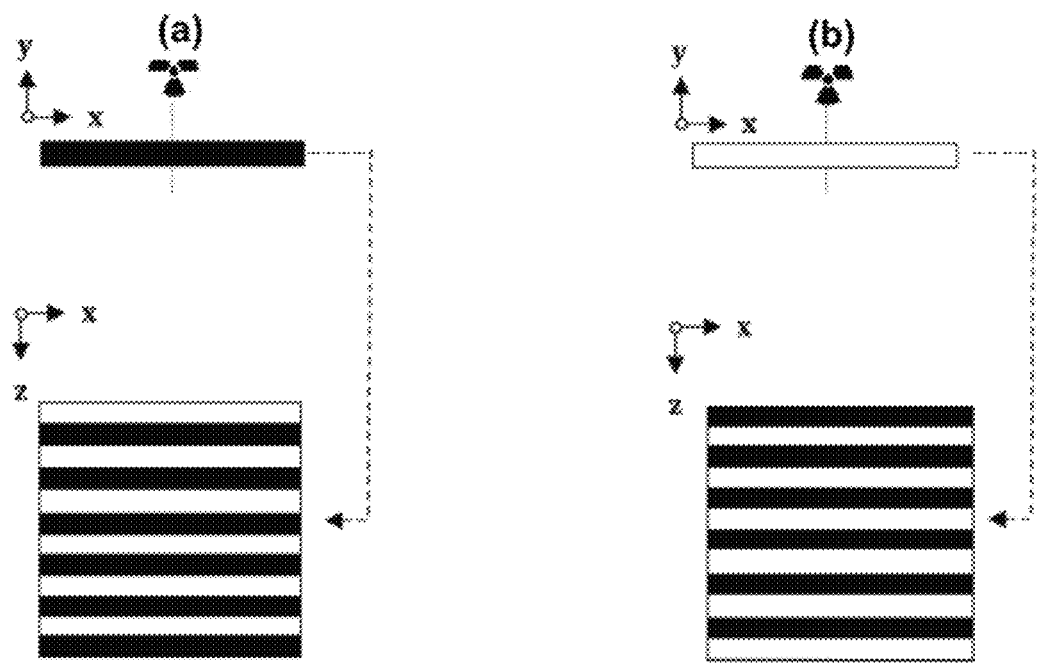
FIGS. 5a-5c show examples of changing blockers in between acquisitions, according to one embodiment of the invention.
Figure 5:
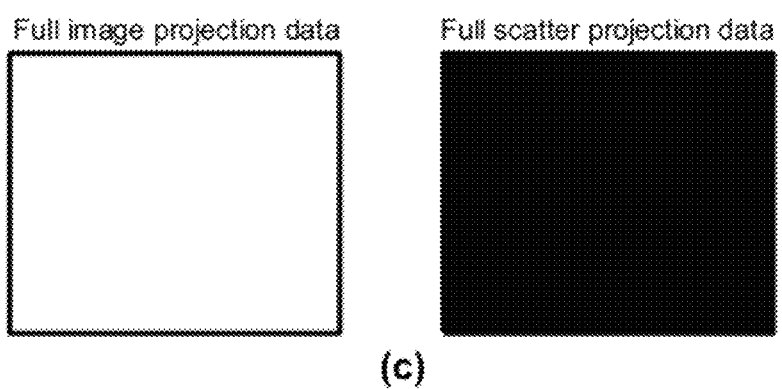

According to another embodiment, the invention includes changing blockers in between acquisitions, where as in producing a movable blocker may be technically complicated, in this embodiment, a partial or full scan is acquired by one blocker, then another or multiple other scans are acquired after the blocker is moved or replaced by a different blocker with a different pattern. FIGS. 5a-5c show examples of such a method in which first one scan is acquired with a transverse blocker, then either the same blocker is moved in the z-direction by the appropriate amount relative to the source or another blocker with a different pattern as shown in FIG. 5b is put in place, and another scan is acquired. Then the data from these two scans can be combined to form a complete image projection and scatter data set across all slices.

According to a further embodiment, the invention includes using relative motion induced by source focal spot position variation and/or source motion, where in place of, or in combination with, moving the blocker, relative motion between the blocker and the source is introduced by source motion or variation in the source focal spot location resulting in relative variations in the illuminated and blocked regions. By means of example and not exclusion, this may include the use of flying focal spot technology (e.g., as utilized in some scanners by Siemens) in which the location of the focal spot in the x-ray tube is electronically varies, or a method where the actual source is moved, or the use of inverse geometry CT type sources (and also electron beam CT systems) which can produce source emanations at different locations. In all such embodiments, the central idea is to produce relative sequential or continues motion between the source and blocker(s) resulting in different illumination regions and patterns and then processed as mentioned throughout this work.

Figure 6:
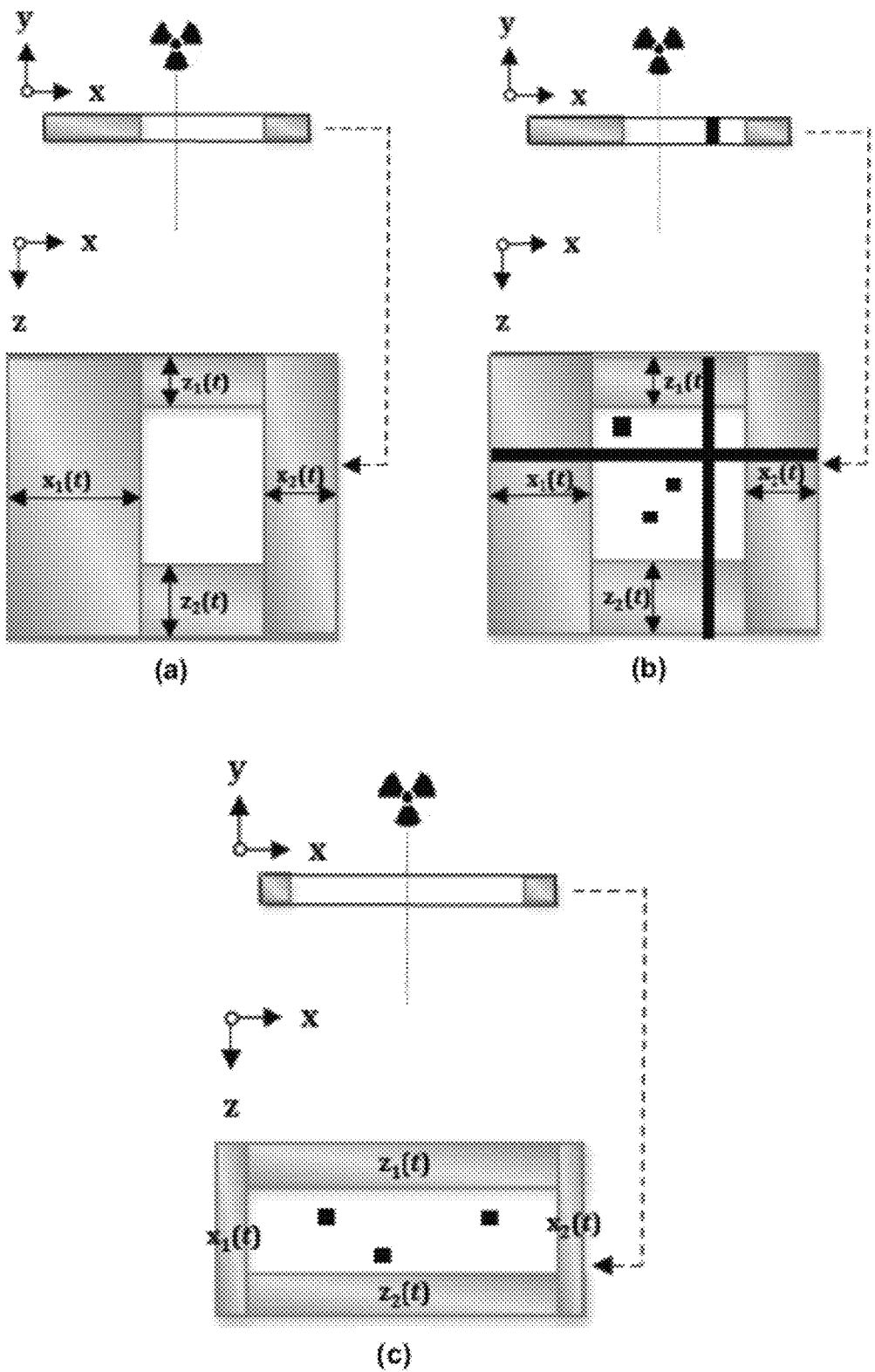
FIGS. 6a-6d show schematic drawings of using source collimator blades/jaws, according to some embodiments of the invention.
Figure 6:
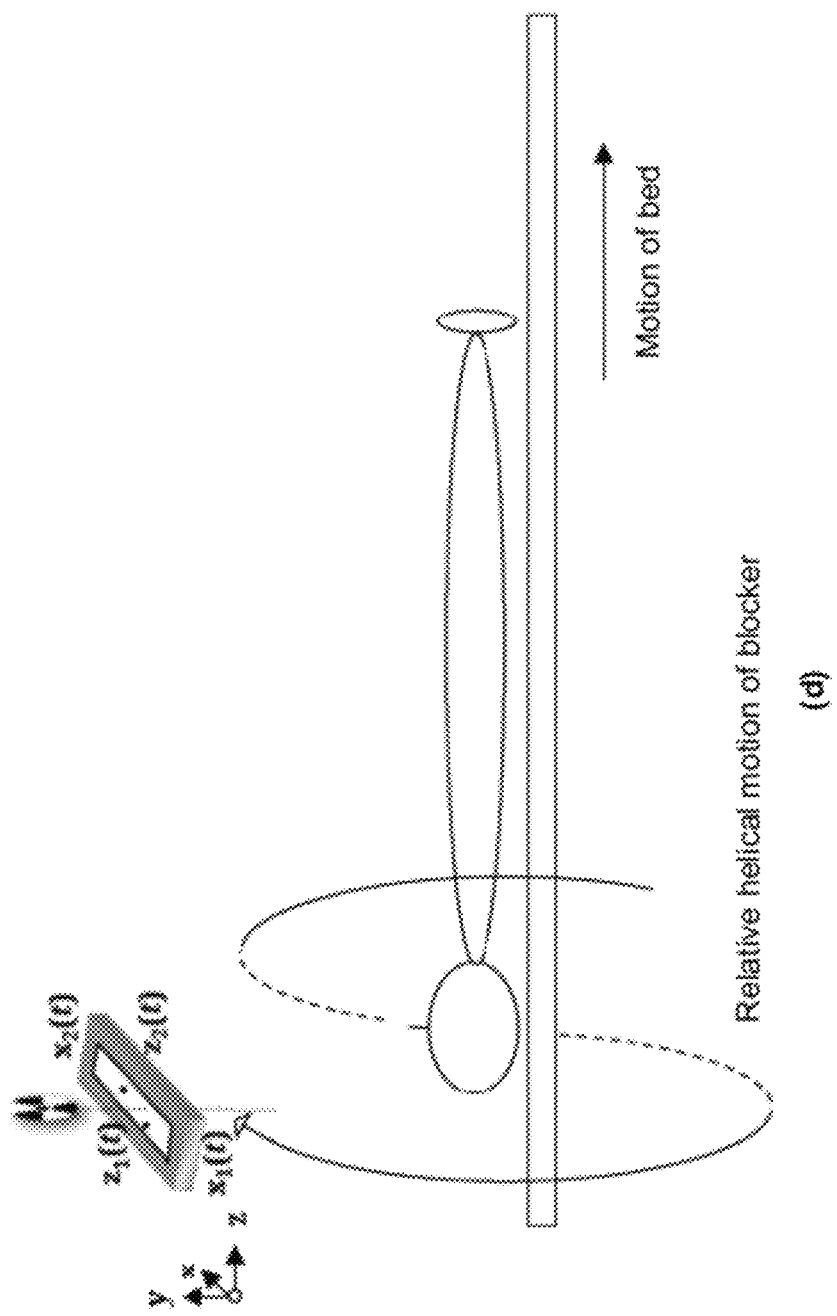

A further embodiment of the invention, shown in FIGS. 6a-6d, includes use of radiation source collimator blades as blockers for scatter detection, where radiation systems such as modern x-ray sources, come with built-in collimator blades/jaws, which serve the purpose of blocking the source to a limited field of view, such as a rectangular area as shown in FIG. 6a. An example of such a system is the Varian True-Beam STx's on board kV x-ray imager, which contains a set of lead collimators that can be set by the user. This technology is conventionally developed for other purposes, such as to limit the imaging area/the area which the patient is exposed to radiation. However here, as a practical embodiment of the blocker scatter correction method, it uses these collimator blades for the new purpose of partially blocking the beam and then detecting the scatter data in the blocked region, which then is used for scatter correction in the image reconstruction or other purposes. Examples of the general method include embodiments where the collimators blades are in a static setting during the scan, or embodiments where the blades are moved in a coordinated/synchronized manner with the movement of the gantry and the couch, as schematically shown in FIG. 6a with the time variable, t, which indicates that the collimator blades are a function of time/a synchronization clock. Additional external blockers as previously described, can be used simultaneously, and synergistically combined with the collimator blades as shown in FIG. 6b to provide additional regions for scatter measurement; these blockers can, for example, be attached to a separate radiolucent stage underneath the source, and they can move in a coordinated fashion as well. Additionally, new collimator blades can be provided in which instead of having a uniform blocking plate, they include general blocking patterns, a variety of which have been shown in this disclosure, for the purposes such as automated and improved scatter detection.

As an example, in FIG. 6a, only the boundaries of the field of view are blocked. Then using interpolation, extrapolation, or compressed sensing techniques, the scatter is approximated throughout the unblocked volume. This method yields the advantage that most of the field of view is unblocked, and after the approximated scatter is subtracted, the reconstruction can be performed by any reconstruction algorithm in the art. This method has been fully implemented by the inventors. Furthermore, systems can be designed with different detector rows at the boundary for the specific detection of the scatter data; since the scatter is low-frequency, cheaper and courser detector elements can be used in these regions.

Regarding cross-sectional reconstruction of the scatter distribution, using the blockers, and above correction method of the current invention, an important embodiment is the production of an imaging modality for reconstructing and displaying the cross-sectional scatter signal throughout an imaging subject. Referring to a design similar to FIG. 6b for example, the method includes subtracting uncorrected CT reconstruction slices having the combination of the scatter and primary signal from the corresponding scatter corrected CT slices derived from said embodiments, to arrive at a cross-sectional image of the scatter-distribution across the imaging subject volume specific.

Referring to a design similar to FIG. 6b for example, a method of producing jointly producing scatter-corrected CT images and displaying the cross-sectional scatter signal throughout an imaging subject, comprises of the following: for a limited select number of slices where scatter signal is available by the means of blocking (the slices in between the block regions), subtracting uncorrected CT reconstruction select slices including the combination of the scatter and primary signal from the corresponding scatter corrected CT slices derived from the embodiments, to arrive at a cross-sectional scatter-distribution across the at the said limited number of slices; using interpolation, extrapolation, and or compressed sensing, on the limited slices to arrive at cross-sectional scatter distribution approximated other slices throughout the rest of the volume, to arrive at an approximated three-dimensional cross-sectional distribution of the scatter; subtracting the approximated three-dimensional cross-sectional distribution of the scatter from the uncorrected cross-sectional CT reconstruction containing both primary and scatter signal, to arrive at a scatter corrected CT reconstruction.

According to one variation of the invention, the scatter data in the various embodiments can be obtained partially, or sparsely. This may be a preferred as the scattered data is low frequency, and thus, from a limited number of detections, the full scatter data can be approximated using interpolations, prior knowledge from physical models, Monte Carlo calculations, or methods for reconstructing sparse data such as compressed sensing and constrained optimization methods. An example of using partially experimental and a partially model-based method is the following: as shown in FIG. 6c for a typical diagnostic multi-detector CT scanner, the blades block the superior and inferior borders, through which scatter data is acquired in the shadow regions at corresponding locations at each gantry angle, which represents the scatter in the superior and inferior slices; it is possible to have additional blockers in the middle of the illuminated field for quantification of the scatter at selected locations in the field. Using this data, several techniques can then be used to derive at an approximation of the scatter data in the central unblocked regions. These methods can included interpolation of the data at the edges, compressed sensing in conjunction with prior knowledge, or Monte Carlo or analytical modeling based on an initial reconstruction of the uncorrected projection data (for example, from the experimental data at the edges, scatter kernels are derived, which then are convoluted with the unblocked projection data, to yield a first approximation of the scatter in the unblocked regions). Once the approximated scatter data throughout the whole field of view is derived at through the methods, then the projection data can be corrected, and reconstructed. This type of partial blocking may be ideal, as it allows for less of the projection data to blocked, leading to more accurate reconstruction of the image data, which is high frequency in contrast to the scatter data.

A further variation is shown in FIG. 6d, in which a combination of the blade collimation, the stated sparse sampling of the scatter data, and stated scatter recover algorithms are used in typical helical CT scanners. Using helical scanning, allows for increased detection of scatter data over the trace of the blocked trajectory regions, which can be utilized for improved scatter modeling. This may be especially relevant to emerging diagnostic multi-detector CT scanners, which are trending towards larger field of views, and hence require a scatter correction method.

Other embodiments of the invention include alternative source trajectories in combination of the blocking methods, examples of which include half-fan method commonly used in CBCT, non-isocentric and off-axis trajectories, non-uniform/exotic helical trajectories. Finally, since planar radiographic imaging (i.e., non-tomographic imaging, such as a chest radiograph, mammography) in essence constitutes the simple analogous acquisition of a single projection, the methods in this invention can accordingly applied to planar radiographic imaging modalities.

According to the invention, a half beam blocker-based embodiment is provided, in conjunction with a total variation regularized Feldkamp-Davis-Kress (FDK) algorithm, to correct scatter-induced artifacts by simultaneously acquiring image and scatter information from a single-rotation CBCT scan. Here, a half beam blocker is provide that includes lead strips, and is used so as to simultaneously acquire image data on one side of the projection data and scatter data on the other half side. 1D cubic B-Spline interpolation/extrapolation is applied to derive patient specific scatter information by using the scatter distributions on strips. The estimated scatter is subtracted from the projection image acquired at the opposite view. With scatter-corrected projections where this subtraction is completed, the FDK algorithm based on a cosine weighting function is performed to reconstruct CBCT volume. To suppress the noise level on the reconstructed CBCT images produced by geometric errors between two opposed projections and interpolated scatter information, total variation regularization is applied by a minimization using a steepest gradient decent optimization method. The experimental studies using Catphan 504 and anthropomorphic pelvis phantoms were carried out to evaluate the performance of the proposed scheme.

The scatter-induced shading artifacts were markedly suppressed in CBCT using the method of the current embodiment. Compared with CBCT without a blocker, the non-uniformity value was dramatically reduced from 46.1% to 4.7%. The root mean square error relative to values inner the regions of interest selected from a benchmark scatter free image was reduced from 50 to 11.3. Also, the proposed approach showed the contrast-to-noise ratio with spatial resolution comparable to the benchmark image. An asymmetric half beam blocker-based FDK acquisition and reconstruction technique is provided. The current embodiment enables simultaneous detection of patient specific scatter and complete volumetric CBCT reconstruction without additional requirements such as prior images, dual scans, or moving strips.

To obtain a high quality CBCT imaging in a single scan without additional requirements such as prior images, dual scans, or moving strips, one embodiment of the invention provides an asymmetric half beam blocker-based image acquisition and reconstruction method based on a total variation (TV), regularized Feldkamp-Davis-Kress (FDK) algorithm. The proposed approach allows simultaneous measurement of the scatter and image data by acquiring a projection image that consists of two parts: unblocked regions on the half side and partially blocked regions on the other half side due to the use of the half beam blocker. This unique configuration makes it possible to obtain the scatter-corrected projection data by subtracting the estimated scatter map in projection image acquired at the opposite view, which is created by interpolation/extrapolation using the scatter distributions on the lead strips in the half side affected by the blocker. With scatter-corrected projections, the FDK algorithm based on a cosine weighting function is performed to reconstruct a CBCT volume. An iterative regularization process is applied to suppress the noise level on the reconstructed images. The effectiveness of the proposed scheme is demonstrated by both Catphan 504 and anthropomorphic pelvis phantoms.

Figure 7:
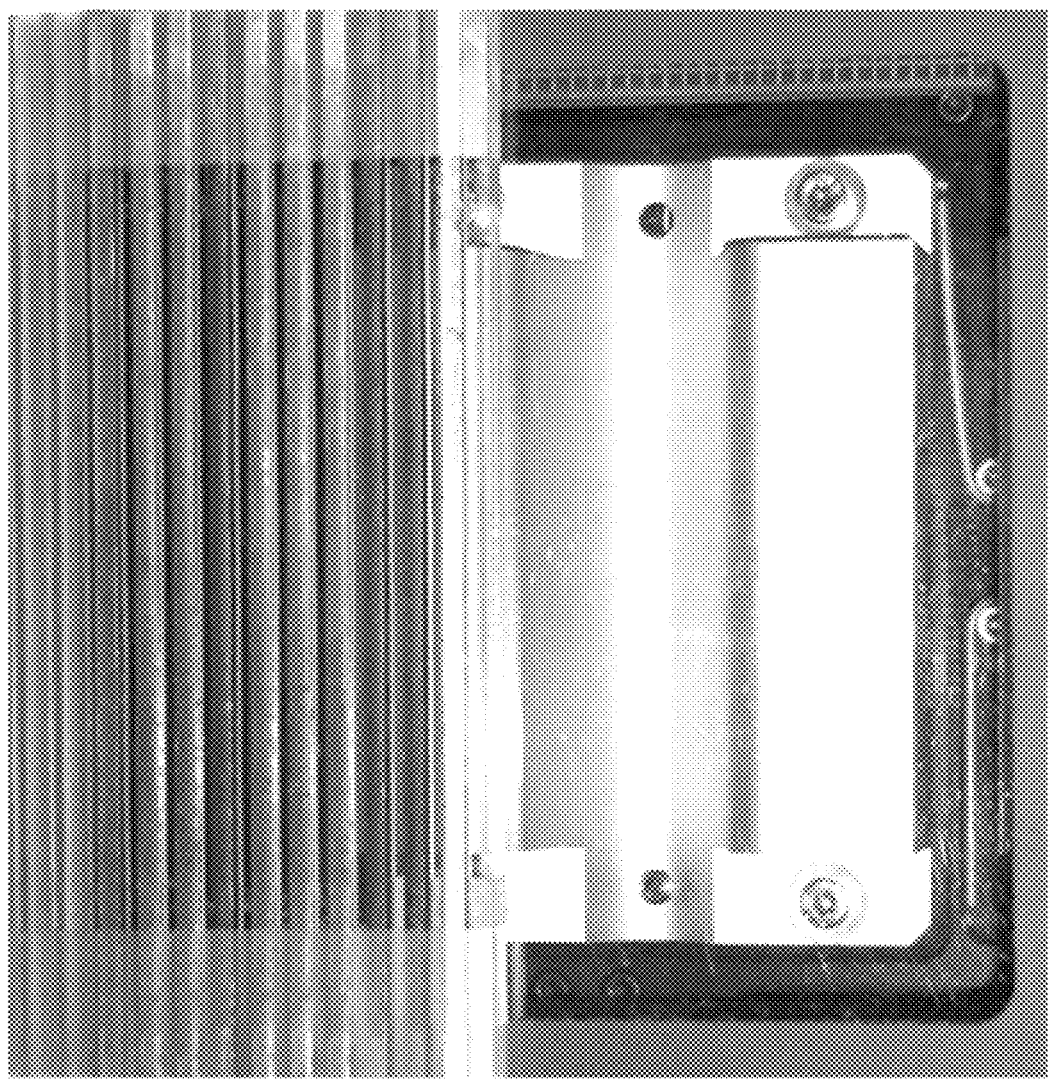
FIG. 7 shows lead strips and a geometric setup of the beam blocker for CBCT imaging, according to one embodiment of the invention.

A half beam blocker embodiment to simultaneously obtain image and scatter information is provided. FIG. 7 shows an embodiment of lead strips and the geometric setup of the beam blocker for CBCT imaging. The lead strips are aligned in the vertical direction and are asymmetrically designed so that the shaded regions are captured wider than the unshaded regions. The strips had a thickness of approximately 3 mm to block penetration of x-ray over 99%. A width of strip and a gap between asymmetric strips were approximately 3 mm and 1.5 mm, respectively. With such a design, a beam blocker having asymmetric lead strips parallel to axial direction of the detector was mounted shifted to the left on the outside surface of the kV x-ray source of the On-Board Imager (OBI) integrated with the TrueBeam linear accelerator (Varian Medical Systems, Palo Alto, Calif.) so that it can influence a half region only in each projection image. When the gantry rotates around the patient's couch, a series of projections is taken along equally spaced angles covering 360° under full fan mode with a bow-tie filter. The number of projections for a full scan is 656. The dimension of each projection acquired on the detector is 397.312×297.984 mm$^2$, containing 1024×768 pixels. The distances of source-to-detector, source-to-axis, and source-to-blocker are 1500 mm, 1000 mm, and 245 mm, respectively. The x-ray tube current was set to 80 mA and the duration of the x-ray pulse was 25 ms during each projection data acquisition. The tube voltage was set to 125 kVp.

Figure 8:
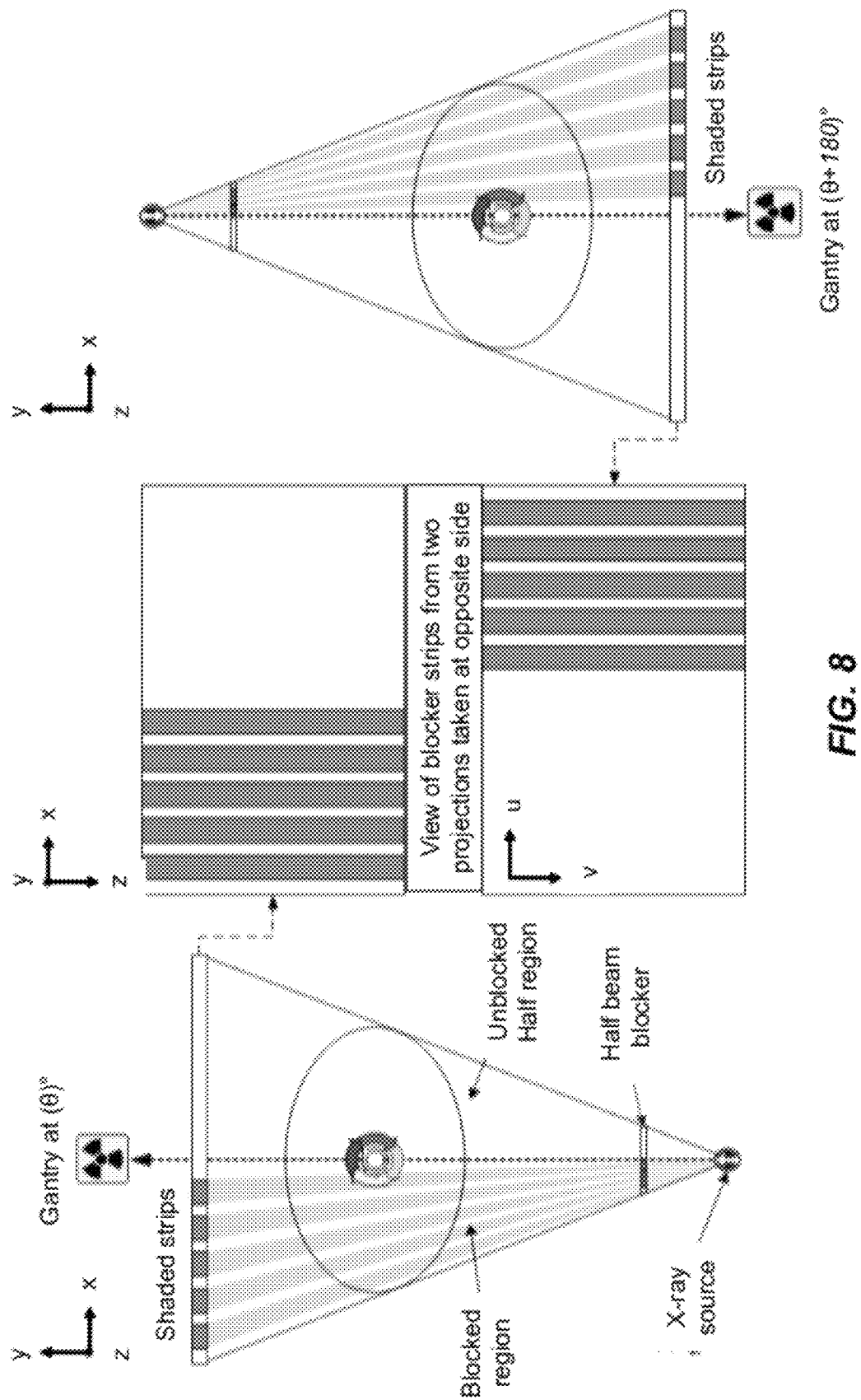
FIG. 8 shows a schematic drawing of the half beam blocker to simultaneously obtain the image data and the scatter data using two projections taken at opposite views, according to one embodiment of the invention.

FIG. 8 shows a schematic drawing of the half beam blocker to simultaneously obtain the image data and the scatter data using two projections taken at opposite views. In each projection frame, the detected information in shaded regions within a half side obstructed by the beam blocker is attributed to the scatter data and that in the unshaded regions within the other half side is the image data (which includes the primary and scatter information). Based on these characteristics, the scatter corrected data at the current view is calculated using the image data at the current view and the scatter data at the opposite view. In practice, it is not easy to exactly estimate the scatter information because of the complex nature of scattering process. However, due to the fact that the point spread function of the scatter is typically smooth and scatter distributions are insensitive to small deformations, these approximations using the scatter information estimated from opposite views make it possible to suppress the scatter-induced artifacts.

Figure 9:
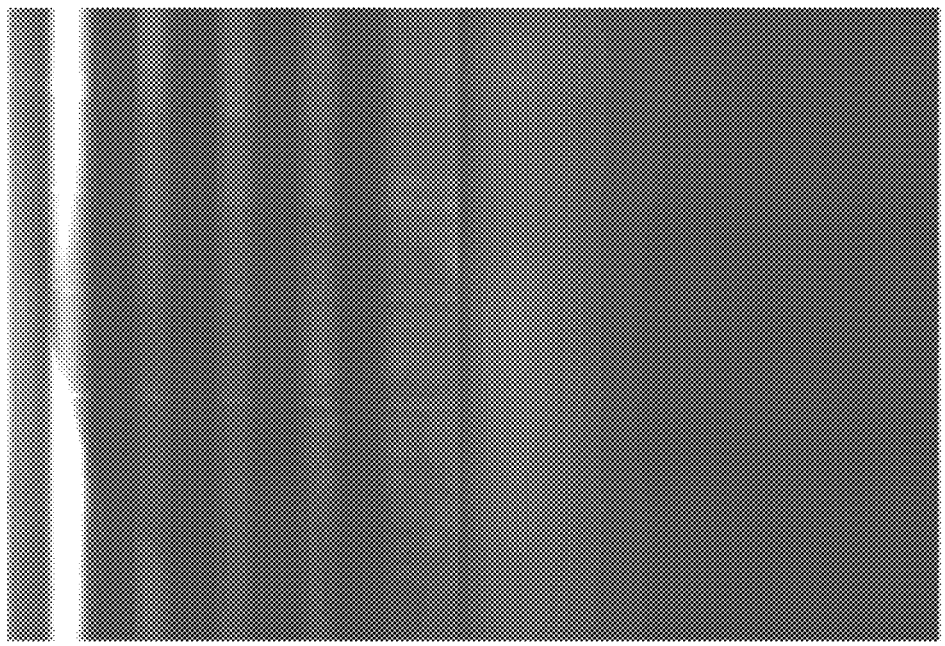
FIG. 9 shows a half region in one projection image with the sum of primary and scatter information and the estimated scatter map to be interpolated using the scatter data inside the central one-third of each shaded region, according to one embodiment of the invention.

Using the scatter data on a partially blocked half region, a 1-D cubic B-Spline interpolation is applied in lateral direction to approximate missing scatter information in unshaded regions of half side. To avoid the penumbra effects caused by x-ray direction and the thickness of a strip, the regions adjacent to the edges of the strip are excluded from the scatter estimation. The average value of the scatter data inside the central one-third of each shaded region is thus considered as a represented control point for 1-D cubic interpolation/extrapolation calculations. By manipulating these represented control points, underlying values are approximated in all pixels within a projection image. This interpolation process can generate an accurate estimate of the scatter because of the assumption that the scatter is smooth within a projection. A moving-average filtering with a width of detector pixels is then applied in the vertical direction to further smooth the scatter distribution. FIG. 9 shows a half region in one projection image with the sum of primary and scatter information and the estimated scatter map to be interpolated using the scatter data inside the central one-third of each shaded region.

Here the cubic B-Spline function interpolates using four control points nearest from a sampling point. There is no need to clip the output to the maximum value and being less than 0 because the sum of control points is 1. When each lateral line within half region of a projection image is composed of several control points where interval between points is $g_x$, an interpolated value I(x) of a sampling point x is calculated as $$I(x) = \sum_{p=0}^{3} B_p(s)\phi_{i+p},$$

where $i=[x/g_x]-1$, $s=x/g_x-[x\,g_x]$ and $\phi_i$ is a control point. $B_p$ corresponds to 1-D cubic B-Spline basis functions as follows:

$B_0(s)=(1-s)^3/6,$ $B_1(s)=(3s^3-6s^2+4)/6,$ $B_2(s)=(-3s^3+3s^2+3s+1)/6,$ $B_3(s)=s^3/6.$

Figure 10:
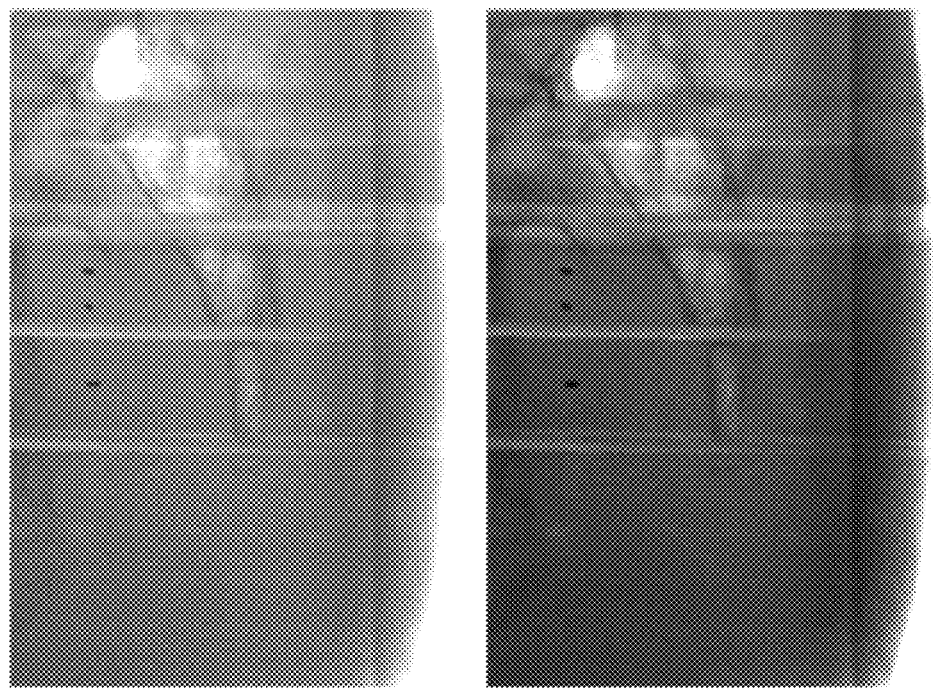
FIGS. 10a-10b show the scatter corrected projection data is obtained by subtracting the estimated scatter map at the opposite projection view from the image data of the current projection view, according to one embodiment of the invention.

The estimated scatter map described above is served for scatter corrected data ($\hat{P}_j$), which subtracts it from the image data of projection image acquired at the opposite view as $$\hat{P}=P(\theta,L-u,v)=P(\theta,L-u,v)-S((\theta+180°)\%360°,u,v)$$

where $P(\theta,L-u,v)$ is measurement value at horizontally-flipped position of $(L-u, v)$ in a given projection of angle $\theta$ where L means the width of each projection image. $S((\theta+180°)\%360°, u, v)$ is the estimated value at position of $(u, v)$ in scatter map within a projection of an opposite angle. By subtracting the estimated scatter map at the opposite projection view from the image data of the current projection view, the scatter corrected projection data is obtained as shown in FIGS. 10a-10b.

According to the current embodiment, reconstruction based on a cosine weighting function using scatter-corrected projections is provided. With the scatter-corrected projection data that apply circular pre-weighting factor on each log-transformed projection data for avoiding the intensity dropping due to the cone angle effect, a 1-D ramp filter is applied to suppress the highest spatial frequency. For the ramp filter, a modified filter with the product of Shepp-Logan filter and raised cosine window function on the frequency domain is provided. The modified filter is expressed as $$H(\omega) = \left|\sin\frac{\omega}{2}\right|(0.515+0.485\cos\omega), -\pi < \omega < \pi.$$

Each horizontal line in preweighted projection data is converted to the frequency domain by one-dimensional Fourier transformation and the Fourier transformed horizontal line is multiplied by the modified filter. By inverse Fourier transformation, filtered projection data with the reduced impulse noise is obtained.

Note that when half regions only are normally used for reconstruction, this FDK-type approach leads to point artifacts in the center area because of abrupt differences between unblocked and blocked regions. In addition it results in the insufficiency in the total object density arising from a greatly reduced number of contributing ray sums. To minimize these problems, a cosine weighting function is applied on all the filtered projections as $$C(u) = \begin{cases} 0 & -L \le u < -\sigma \\ \cos\left(\frac{u-\sigma}{2\sigma}\pi\right)+1 & -\sigma \le u \le \sigma \\ 2 & \sigma < u \le L \end{cases},$$

where the rotation axis is at the origin and the measured projection image occupies the width $-L \le u \le L$. The degree of smoothing is dependent on a parameter $\sigma$ (set to 30 pixels that are a half of the length of the shadow region caused by the lead strips in each projection image) and worsens to a singularity as a approaches zero. It can be expressed by multiplying the cosine weighting function on filtered projection $\bar{P}(u, v)$ data, as $$\tilde{P}(u,v) = C(u) \cdot \bar{P}(u,v).$$

Figure 11:
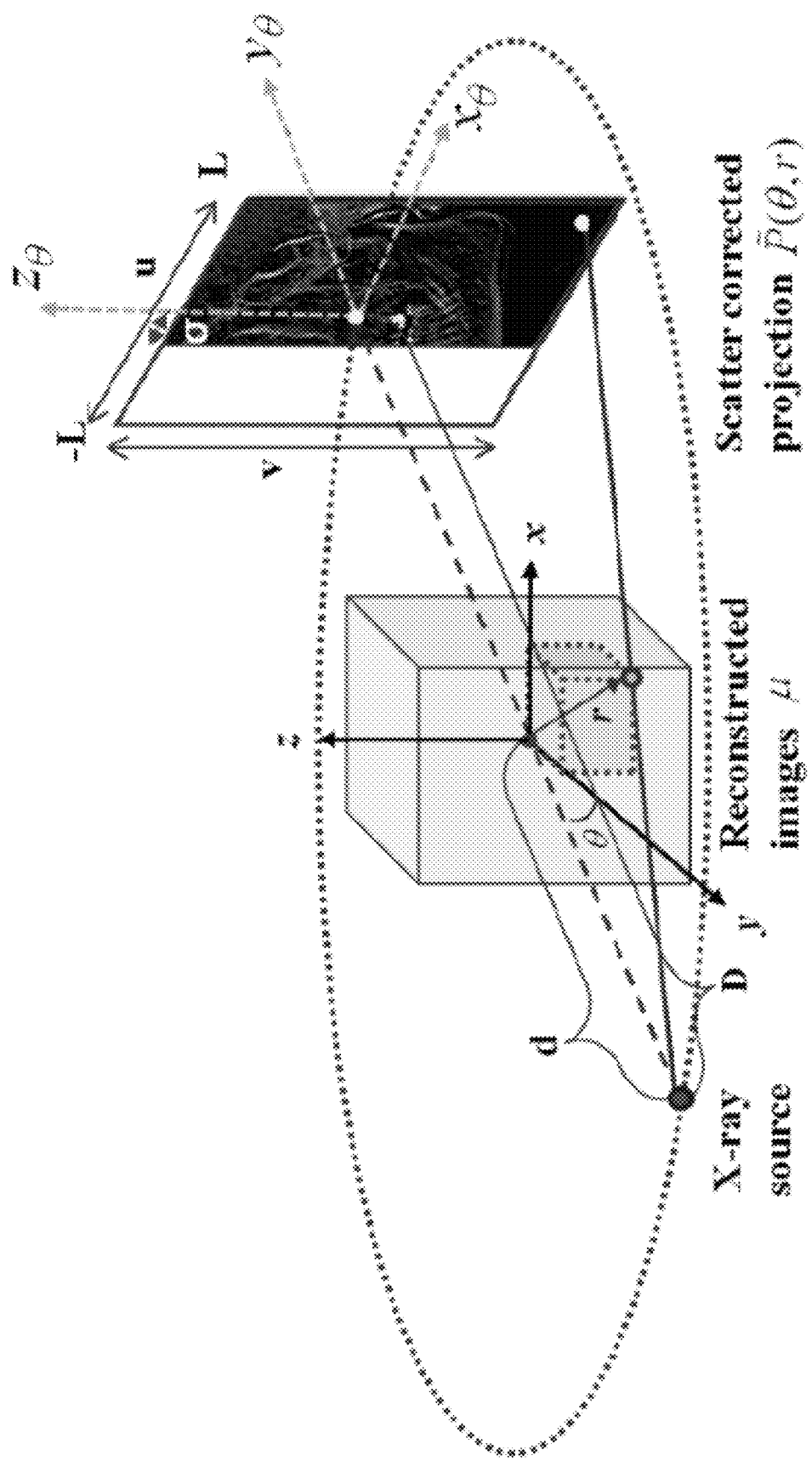
FIG. 11 shows the geometric information of the scatter corrected data and notations for backprojection calculation, according to one embodiment of the invention.

With filtered projection data where the cosine weighting function is applied, the averaging filtering method with a mask size of 3×3 is carried out to mitigate any impulse noise that may remain in the data. After this averaging operator is done, a back projection step is performed to reconstruct a complete CBCT volume. FIG. 11 is to show geometric information of the scatter corrected data and notations for backprojection calculation.

Here, back projection for the FDK algorithm includes, given a position vector r or $(r_x, r_y, r_z)$ of any voxel, projected position $(u(r), v(r))$ can be calculated as $$\tilde{P}(\theta, r) = \tilde{P}(\theta, u(r), v(r)),$$

where $$u(r) = \frac{r_{x\theta}}{d+r_{y\theta}}D,$$

$$v(r) = \frac{r_{z\theta}}{d+r_{y\theta}}D.$$

Here d is the source-to-axis distance and the rotate vectors $[r_{x\theta}, r_{y\theta}, r_{z\theta}]^T$ are calculated by applying the rotation matrix through a given angle $\theta$ from the origin of the reconstruction images as $$\begin{pmatrix} r_{x\theta} \\ r_{y\theta} \\ r_{z\theta} \end{pmatrix} = \begin{pmatrix} \cos\theta & -\sin\theta & 0 \\ \sin\theta & \cos\theta & 0 \\ 0 & 0 & 1 \end{pmatrix}\begin{pmatrix} r_x \\ r_y \\ r_z \end{pmatrix}.$$

the final attenuation coefficient value $\mu(r)$, at a position vector r is weighted and accumulated as follows:

$$\mu(r) = \mu(r_x, r_y, r_z) = \frac{\pi}{N}\sum_{n=1}^{N}\left(w(r) \cdot \tilde{P}_n(\theta, u(r), v(r))\right),$$

$$w(r) = \frac{d^2}{(d+r_{y\theta})^2},$$

where $w(r)$ is the depth weighting and N is the total number of projection data. Every voxel has measurements in all projection data and it is normalized by a uniform factor N in the backprojection step.

Regarding the Total variation (TV) regularization for noise reduction, residual noise can exist in the scatter-corrected projections due to interpolation of the scatter data and possible geometric errors between two opposed projections even though the subtraction is processed. To enlarge the difference between tissue features and unwanted noise in image domain, a TV regularization based on the discrete gradient transform is used. Minimizing the TV objective function of the reconstructed images helps resolve noisy voxels having low contrast. The TV objective function is written as $$R(\mu) = \sum_j G(\mu_j) = \sum_l \sum_m \sum_n G(\mu_{(l,m,n)}) = \sum_l \sum_m \sum_n \sqrt{a^2+b^2+c^2+\delta},$$

where $$a = \mu_{(l,m,n)} - \mu_{(l-1,m,n)},$$

$$b = \mu_{(l,m,n)} - \mu_{(l,m-1,n)},$$

$$c = \mu_{(l,m,n)} - \mu_{(l,m,n-1)},$$

Here, $\mu_{(l,m,n)}$ is the attenuation coefficient at the 3D position (l, m, n) and $G(\mu_j)$ means the discrete gradient transform with forward difference in the j-th indexed value (or (l, m, n)-position) of the reconstructed images. A small constant δ is added to avoid singularity. The TV objective function R(μ) above is minimized by the steepest gradient descent method with an adaptive step size, which is expressed as $$\mu_j^{l+1} = \mu_j^l - \lambda \frac{\Delta R(\mu_j)}{|\Delta R(\mu)|},$$

where $\mu_j$ means the j-th indexed value of the reconstructed images generated by a cosine-weighted FDK algorithm with scatter-corrected projection data. λ is an adaptive parameter that controls the step size so that values updated in each steepest gradient decent step are forced to progressively smaller values with an increase in the number of iterations. This parameter is set to 0.2 initially and this value is linearly decreased by multiplying a constant value ($\lambda_{red}$) if calculated at current iteration step is larger than that at previous one (see the psedo-code in Algorithm A1 below). $\nabla R(\mu_j)$ is the gradient of objective function, at j-th indexed voxel, and $|\nabla R(\mu)|$, the root-sum-square of gradient calculated at all pixels, is necessary for the normalized gradient calculation. For completeness, provided is the expression as $$\Delta R(\mu_j) = \frac{\partial R(\mu)}{\partial \mu_j} = \frac{\partial R(\mu)}{\partial \mu_{(l,m,n)}} =$$

$$\left( \begin{array}{c} \frac{3\mu_{(l,m,n)} - \mu_{(l-1,m,n)} - \mu_{(l,m-1,n)} - \mu_{(l,m,n-1)} +}{G(\mu_{(l,m,n)})} \\ \frac{\mu_{(l,m,n)} - \mu_{(l-1,m,n)}}{G(\mu_{(l-1,m,n)})} + \frac{\mu_{(l,m,n)} - \mu_{(l,m+1,n)}}{G(\mu_{(l,m+1,n)})} + \frac{\mu_{(l,m,n)} - \mu_{(l,m,n+1)}}{G(\mu_{(l,m,n+1)})} \end{array} \right),$$

$$|\Delta R(\mu)| = \sqrt{\sum_j (\Delta R(\mu_j))^2}.$$

The number of iteration for the steepest gradient descent step was set to 30 in the study. The pseudo-code is presented in the following algorithm.

```
λ = 0.2; λ_red = 0.8
for i = 1 to 30 do
    for j = 1 to all pixels do
        ∂μ_j = ∇R(μ_j)

|∇R(μ)| = √(Σ_j (∂μ_j)²)

end for
    for j = 1 to all pixels do
        ∂μ_j = ∂μ_j/|∇R(μ)|
        μ_j = μ_j - λ · ∂μ_j
        if (μ_j' < 0) μ_j' = 0
    end for
    while R(μ') > R(μ) do
        λ = λ × λ_red
        for j = 1 to all pixels do
            μ_j' = μ_j - λ · ∂μ_j
            if (μ_j' < 0) μ_j' = 0
        end for
    end while
    μ = μ'
end for
```

Regarding experimental evaluation, qualitative and quantitative comparisons were performed between FDK reconstructions with and without a blocker using the Catphan 504 and anthropomorphic pelvis phantoms. The Catphan 504 phantom was used with an added elliptical body annulus in the periphery to model the scatter caused by thicker regions of the body, such as the pelvis. The reconstructed images using two phantoms were generated with a size of 352×352×128 voxels, where the voxel size is 0.776×0.776×1.552 mm³.

Comparisons of the reconstructed images were done to illustrate the performance of the proposed method. In the experiments of the Catphan 504 phantom, a benchmark scatter free image was obtained by using a fan-beam multidetector CT (MDCT) scanner. The body annulus was removed to further reduce the scatter. In the quantitative analysis, reconstructed values were converted to Hounsfield unit (HU) in selected regions of interest (ROI) and compared to those in the benchmark image.

To quantitatively evaluate the effectiveness of the proposed method, the contrast-to-noise ratio (CNR) was calculated at selected regions of interest (ROIs) in the reconstructed image. It is possible to assess a comparison of relative image contrast between corresponding regions. The CNR is expressed as $$CNR = \frac{|E_s - E_n|}{\sqrt{\delta_s^2 + \delta_n^2}},$$

where $E_s$ and $E_n$ denote the mean values of the signal and noise. $\delta_s$ and $\delta_n$ are the respective standard deviations of the signal and noise levels.

As a second measure, non-uniformity (NU) of the reconstructed images was evaluated to judge whether scatter-contaminated shading artifacts can be mitigated by the proposed method. The NU can be measured by determining the minimum and maximum HU values within a ROI selected on the region with uniform intensity distribution and by defining as $$NU = \left| \frac{V_{max} - V_{min}}{V_{max} + V_{min}} \right| \times 100\%,$$

where $V_{max}$ and $V_{min}$ denote the maximum and minimum HU values among voxels within a ROI. As a third measure, the accuracy of CT number in selected ROIs was assessed by calculating the root mean square error (RMSE), which is defined as $$MSE = \sqrt{\frac{1}{N} \sum_i (V^i - V_b^i)^2},$$

where $V^i$ denote the mean HU value of the ith ROI. $V_b^i$ is the corresponding value measured in the benchmark image. N is the number of selected ROIs.

Figure 12:
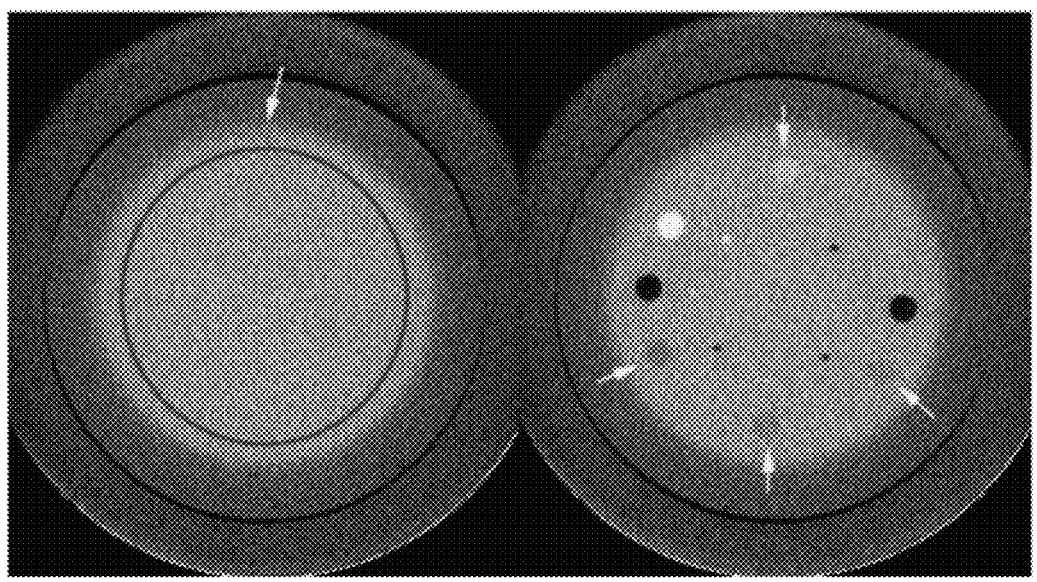
FIGS. 12a-12c show slices of CBCT reconstructions obtained by the described methods and FDK algorithm without a blocker, according to one embodiment of the current invention.
Figure 12:
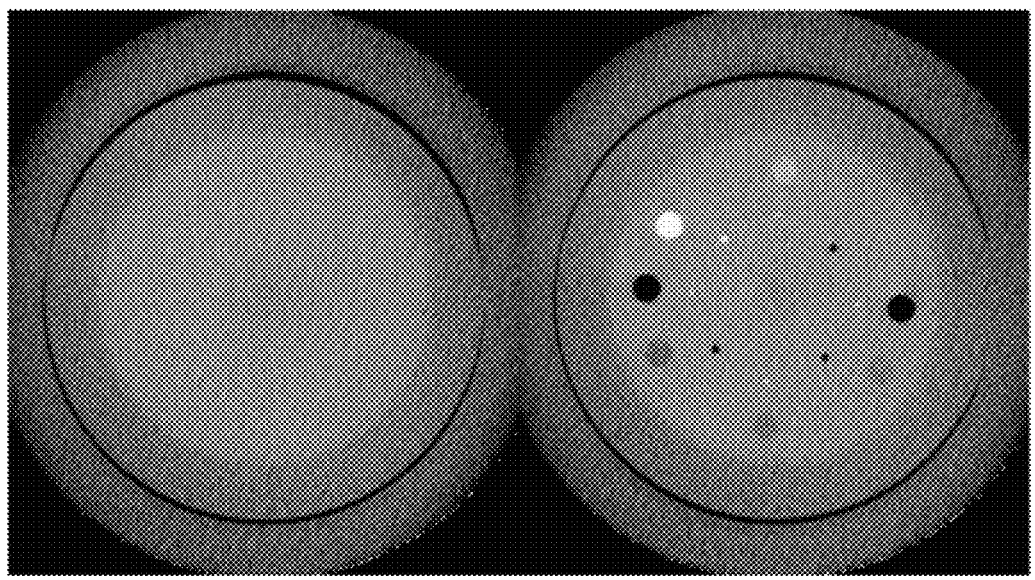
Figure 12:
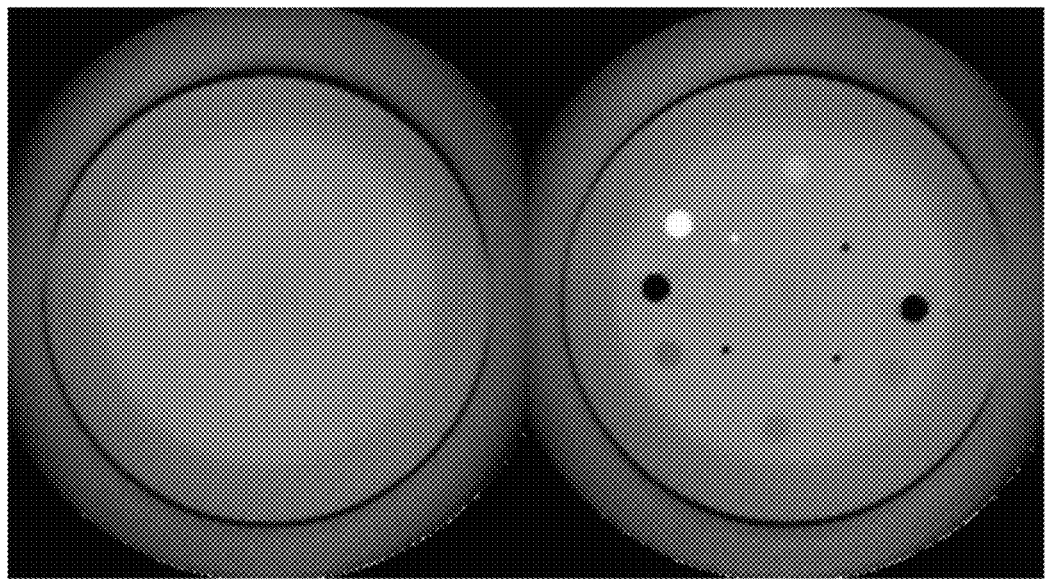
Figure 13:
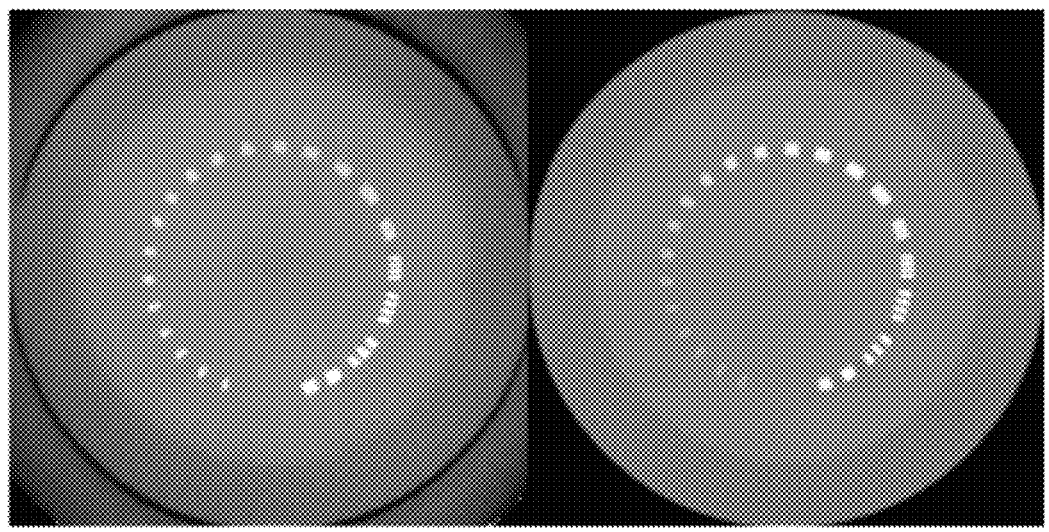
FIGS. 13a-13b show a comparison between one embodiment of the current invention-based reconstruction image and benchmark image.

Regarding the results, FIGS. 12a-12c show the corresponding slices of the CBCT reconstructions obtained by the proposed scheme and FDK algorithm without a blocker. FIG. 12a shows the image reconstructed using the conventional FDK algorithm without a blocker from full projection images that are contaminated by the scatter. It is observed that scatter artifacts cause ambiguous edges between objects with different densities as pointed out to arrows. FIG. 12b shows the reconstruction image generated from the scatter-corrected projection data where the estimated scatter data are subtracted from the image data of the opposite view. Shading artifacts are significantly suppressed, but the noise is increased relative to FIG. 12a. By applying a TV regularization on the reconstructed images of FIG. 12b, it is observed that noises are smoothed while not penalizing striking features heavily, as shown in FIG. 12c. FIGS. 13a-13b are to compare the current invention-based reconstruction image with the benchmark image. The visual quality of image reconstructed by the current invention showed the CNR with spatial resolution comparable to the benchmark image.

Figure 14:
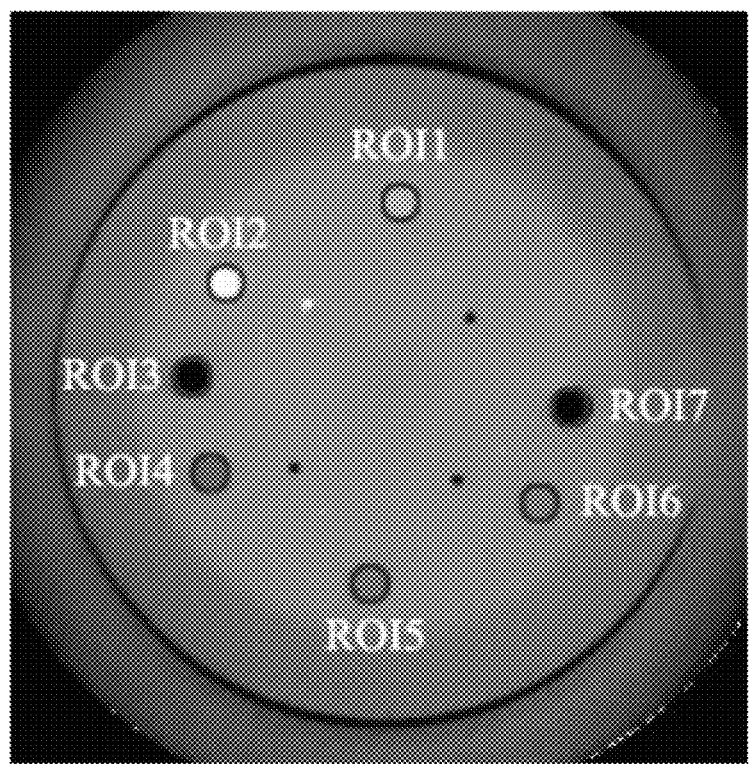
FIGS. 14a-14b show calculated CNR at seven regions of interest (ROIs) in the reconstruction image and the plotted results, respectively, according to one embodiment of the current invention.
Figure 14:
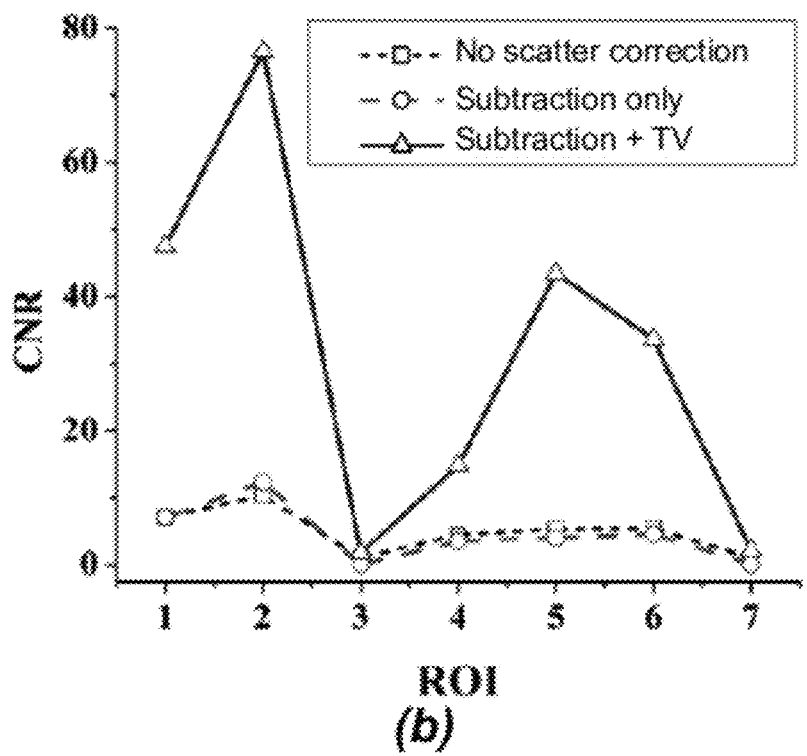
Figure 16:
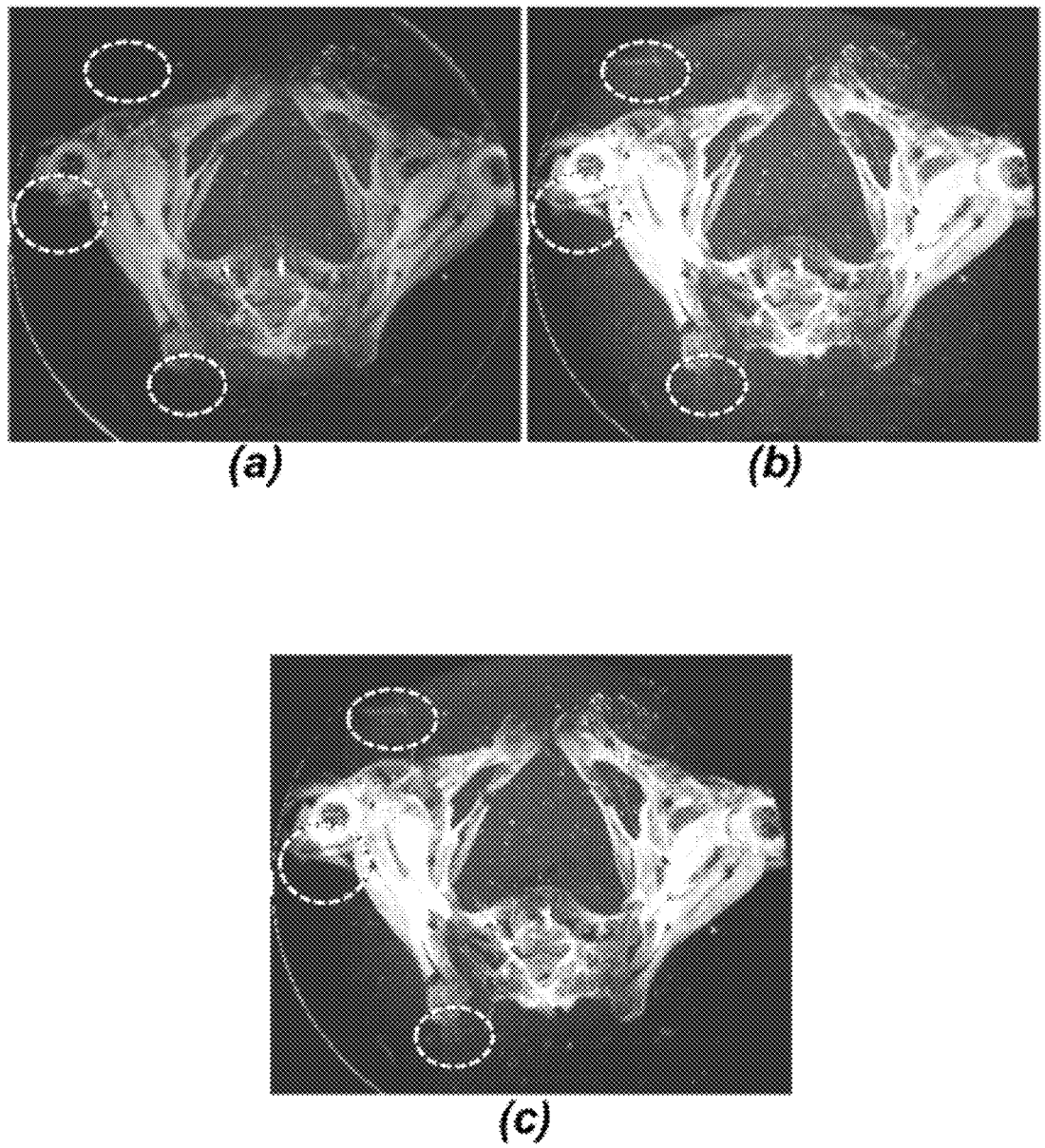
FIGS. 16a-16c show a comparison of a maximum intensity projection (MIP) of the reconstructed images using experimental data, according to one embodiment of the current invention.

FIGS. 14a-14b are to calculate the CNR at seven regions of interest (ROIs) in the reconstruction image and the results were plotted as shown in FIG. 14b. After a TV regularization, the proposed algorithm shows a smoother decrease in all ROIs and thus leads to a better CNR compared to no scatter correction. Table I summarizes the HU values in selected ROIs and RMSE values relative to the values obtained in a benchmark image. Using the proposed half beam based TV regularization technique, it is observed that CT number errors are reduced from 50.0 to 11.3. NU values were calculated on the selected ROI as shown in FIG. 12a. The NU of the image without a blocker is 46.1%. The NU of the image reconstructed by projection data after scatter subtraction is 52.9%. The NU of images reconstructed by a TV regularization is dramatically reduced to 4.7% since the increased noises caused by subtraction process are mitigated. Judging by these quantitative measures, it is noted that the use of a half-beam blocker and a TV regularization has a great effect in mitigating scatter-contaminated shading artifacts as well as the noise level.

an anatomic loss due to a low contrast coming from severe shading in the axial CBCT images, while the current embodiment shows that it is quite apparent in bony structures due to an enhancement in image sharpness coming from a half beam blocker based scatter correction without the anatomic loss. In addition to a TV regularization on the half beam blocker based scatter correction, the quality of reconstructed images is considerably improved while preserving striking features as shown in FIG. 16c.

Turning now to a discussion and conclusions for the current embodiment, an effective image acquisition and reconstruction algorithm has been described for scatter correction in CBCT. The current embodiment includes two novelties: (1) a half beam blocker-based image acquisition allowing for simultaneous measurements of scatter and image information in a single scan and (2) a TV regularization to mitigate the increase of noise levels caused by the interpolated scatter data and geometric errors between two opposed projections.

Reconstructions performed by the current embodiment on Catphan 504 and anthropomorphic phantoms indicate that a higher image quality can be achievable with scatter-contaminated projection data acquired from wide x-ray collimation. It was also found that the proposed half beam blocker scheme shows the CNR with spatial resolution comparable to fan-beam MDCT images. Moreover, the TV regularization gives the reconstruction images with a greatly reduced noise and thus achieves better CNR and NU as well as more accurate CT number. All of these results indicate that the algorithm of the

TABLE I

Comparison of CT number errors in seven ROIs of the Catphan504 phantom

|  | ROI1 | ROI2 | ROI3 | ROI4 | ROI5 | ROI6 | ROI7 | RMSE |
|---|---|---|---|---|---|---|---|---|
| Benchmark image | 345.5 | 932.9 | −971.4 | −174.9 | −87.3 | −35.1 | −981.1 |  |
| No scatter correction | 311.1 | 886.3 | −906.4 | −187.9 | −71.1 | −2.3 | −889.5 | 50.0 |
| Subtraction only | 337.6 | 973.1 | −1020 | −208.2 | −109.3 | −44.1 | −1020.9 | 32.3 |
| Subtraction + TV | 336.2 | 918.9 | −959.8 | −167.5 | −80.4 | −31.8 | −962.2 | 11.3 |

Figure 15:
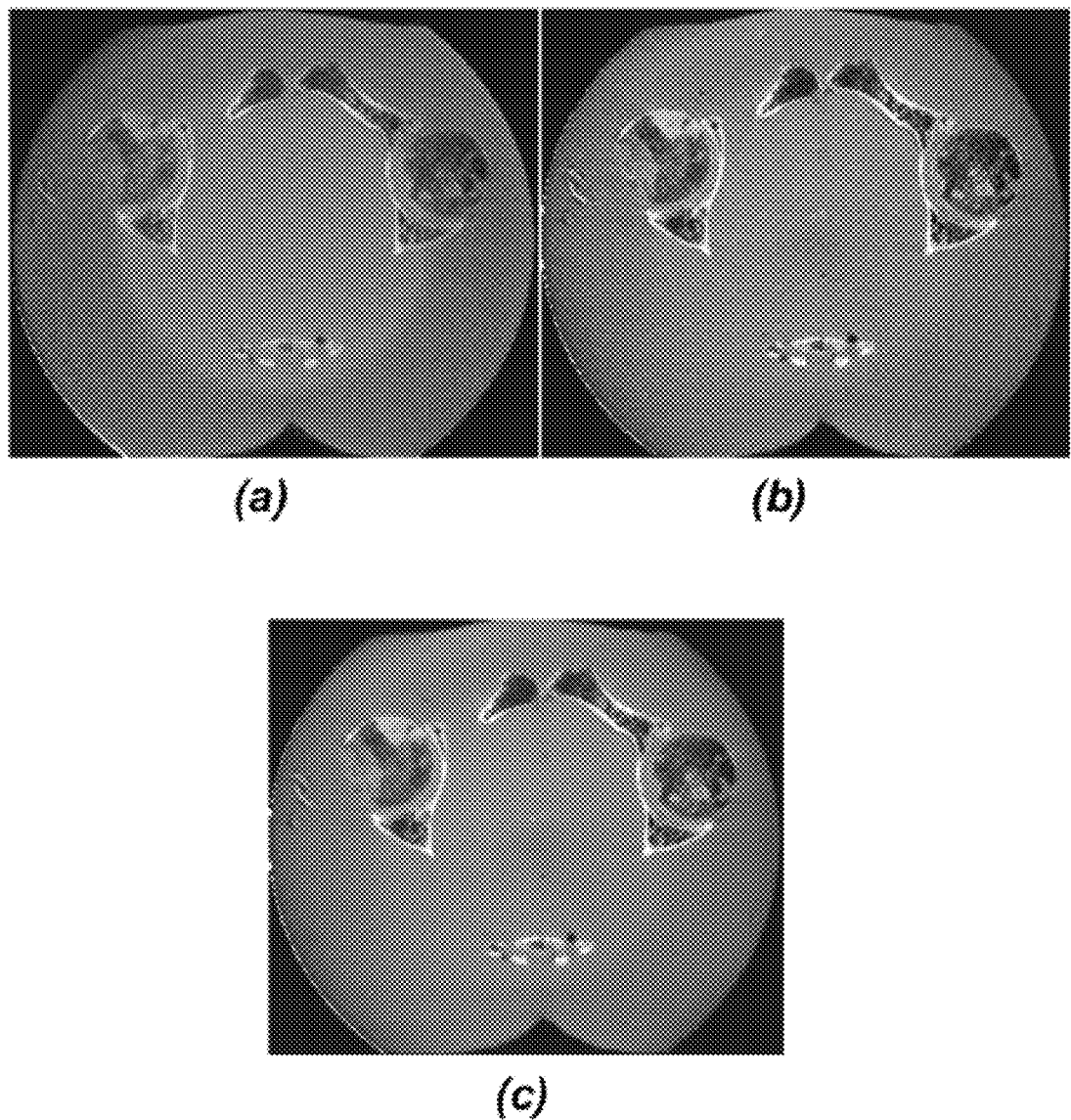
FIGS. 15a-15c show corresponding slices of reconstruction images generated with the pelvis phantom data by a FDK algorithm with no blocker, the half-beam blocker of one embodiment using subtraction only, and the current invention using both subtraction and TV regularization.

FIGS. 15a-15c show the corresponding slices of the reconstruction images generated with the pelvis phantom data by a FDK algorithm with no blocker, the proposed half-beam blocker scheme using subtraction only, and the current invention using both subtraction and TV regularization. As shown in FIG. 15a, severe shading artifacts are observed around the outer regions than in the center of object because there is more attenuation due to the fact that the pelvis phantom to be used is beyond the field of view. On the other hand, the half-beam blocker according to the current invention significantly reduces these shading distortions and provides image sharpness on the anatomic structures and noises, as shown in FIG. 15b. It is observed that a TV regularization mitigates the noise level while disclosing more anatomic structures details, as shown in FIG. 15c. With the same data, a comparison of a maximum intensity projection (MIP) of the reconstructed images is provided as shown in FIGS. 16a-16c. Since an MIP image makes it possible to extract the highest value encountered along the corresponding viewing ray at each pixel of the reconstructed images, it can judged whether bony structures with high contrast are well extracted in the reconstruction images without the interference caused by scatter-induced shading or noises. As marked to circles in FIGS. 16a-16c, it is observed that the non-blocker based FDK algorithm causes current embodiment provides high contrast-to-noise CBCT images by suppressing scatter-induced shading and noise-corrupted regions while not penalizing striking features heavily.

For clinical applications of the scatter-correction algorithm of the current embodiment, a few practical considerations deserve some discussion here. (1) Although a TV regularization has been implemented for optimal reconstruction, it can be readily utilized with standard non-regularized and non-iterative reconstruction algorithms, as demonstrated in FIG. 12c. (2) The parameters for the TV regularization are empirically determined in this study, but they can be automated at least in principle. (3) In this description, it is assumed that the scatter information at the current view is the same as that of the opposite view. While this is exact for parallel beam geometry, it is valid only approximately for cone-beam geometry. Our experimental data demonstrated the validity of the assumption.

Discussing now some conclusions for the current embodiment, a half beam blocker-based image acquisition and reconstruction method for scatter-corrected CBCT imaging has been presented and validated in phantom experiments. The method was demonstrated to substantially mitigate scatter-induced artifacts from a single-rotation scan without additional requirements such as prior images, dual scans, or moving strips. In addition, it allows reducing approximately half the patient dose compared with conventional CBCT without a blocker. The current invention has significant implication in image guided or adaptive radiation therapy as CBCT is used repeatedly.

Figure 17:
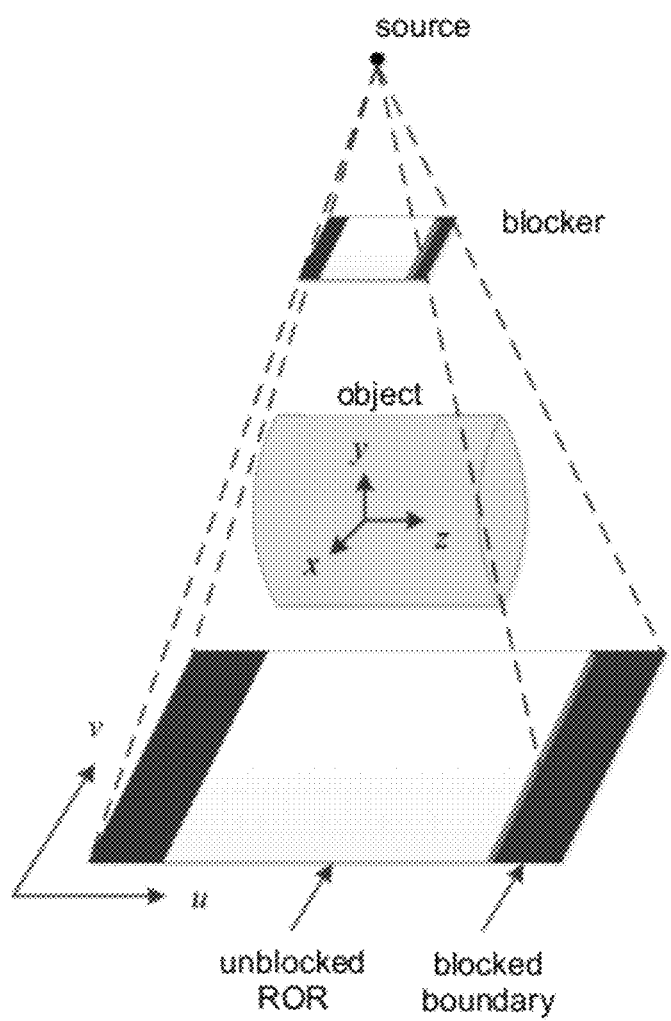
FIG. 17 shows the geometry of the blocker setup, according to one embodiment of the current invention.

FIG. 17 shows the geometry of the blocker setup, according to one embodiment of the current invention. The blocker is inserted between the x-ray source and the patient. It only blocks the two boundaries along the u-direction while the gantry rotates around the z-axis. In FIG. 17, instead of alternating lead strips, which are widely used in various scatter correction schemes, the lead strips are only attached to the two boundaries of the detector along v-direction. This embodiment ensures that the region of reconstruction (ROR) does not lose any projection data and the scatter distribution is only collected on the boundary regions. Unlike scatter correction methods, which require additional scans and thus prolong the treatment time, this scheme integrates the scatter estimation/correction into the projection collection in one scan. Moreover, in many commercial scanners, the boundary blocked region has the "free" projection which otherwise was abandoned. Here, the "free" boundary scatter is effectively utilized to estimate the scatter distribution in the central ROR.

Figure 18:
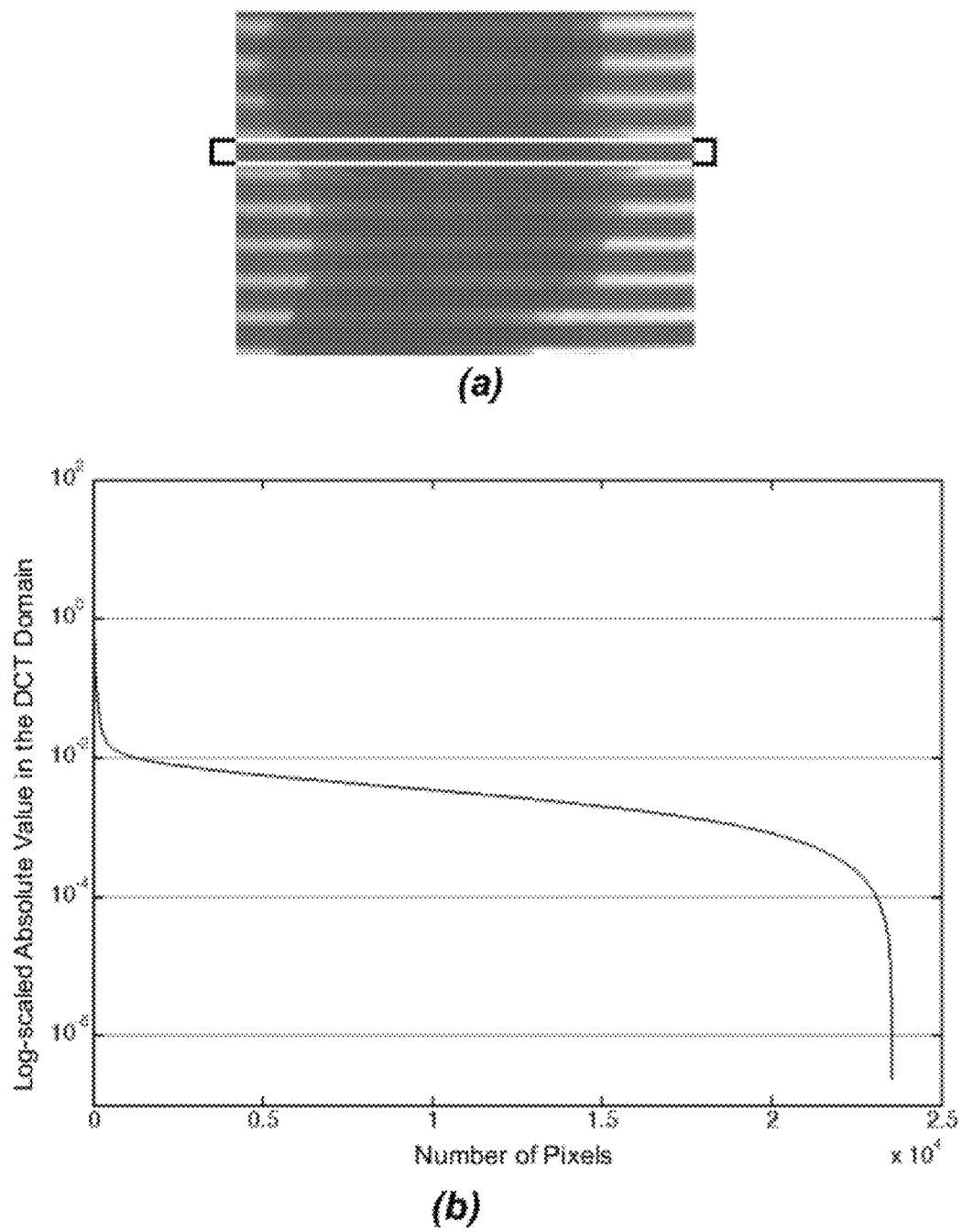
FIGS. 18a-18b show the sparsity of the scatter signal in the DCT domain, according to one embodiment of the invention.

In the current embodiment of the invention, two assumptions are made: 1) Scatter signal is mainly low frequency signal in Fourier domain and it is sparse; 2) Scatter signal can be roughly expressed as the convolution of the primary signal with an anisotropic kernel, and hence scatter signal can be written as a function of the projection. The first assumption is based on the recent findings by the inventors that demonstrate distribution of scatter signals with Monte Carlo (MC) simulations and clinical data. In the current embodiment, the scatter signal is analyzed by using discrete cosine transform (DCT) instead of Fourier Transform (FT) because the former not only translates the signal into a sparse domain, but also maintained it to be real number in both the original domain and the transformed domain, which facilitates the numerical calculation successively in this work. FIGS. 18a-18b show the sparsity of the scatter signal in the DCT domain. In FIG. 18a, one projection of the head phantom with stripped lead blocker was applied to simulate the scatter distribution. The signal in the bracket was after the blocker region and was extracted for the scatter distribution analysis. FIG. 18b shows absolute values of the two dimension log-scaled DCT (DCT2) coefficients for the bracket area in a descending order. The maximum DCT2 coefficient is 14.93, and the number of entries whose absolute values are greater than 0.01 is less than 5.30 percent of the total pixels.

Figure 19:
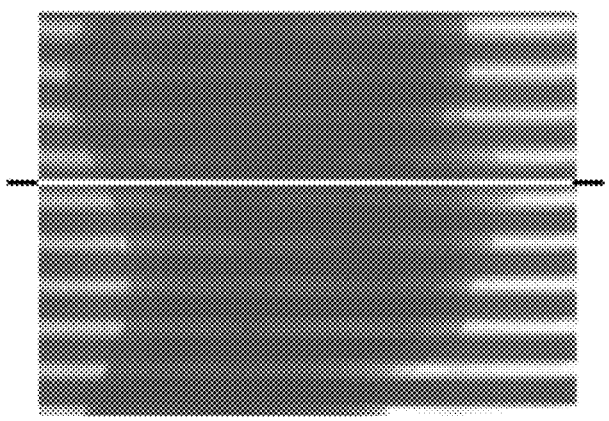
FIGS. 19a-19c show 1-D profiles of the scatter map for the first projection with an interpolation method, a modeled method and one embodiment of the current invention, together with the benchmark, the measured scatter signal.
Figure 19:
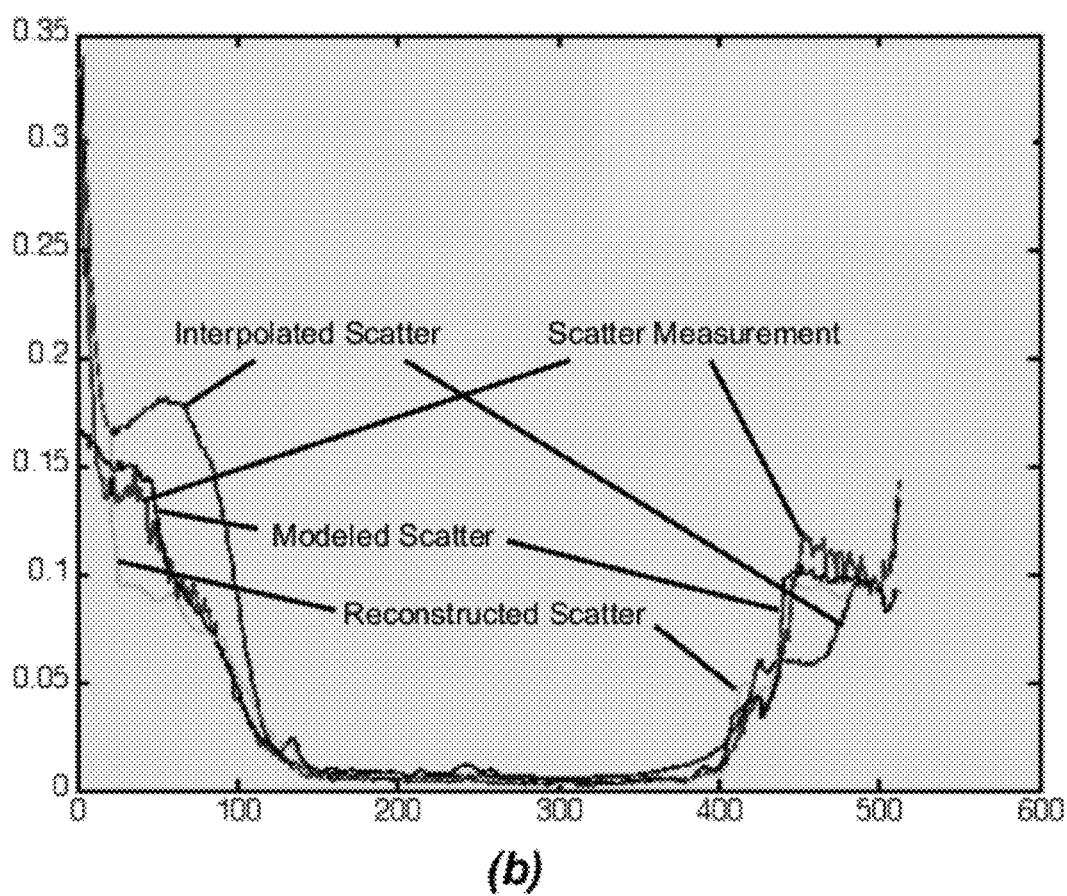
Figure 19:
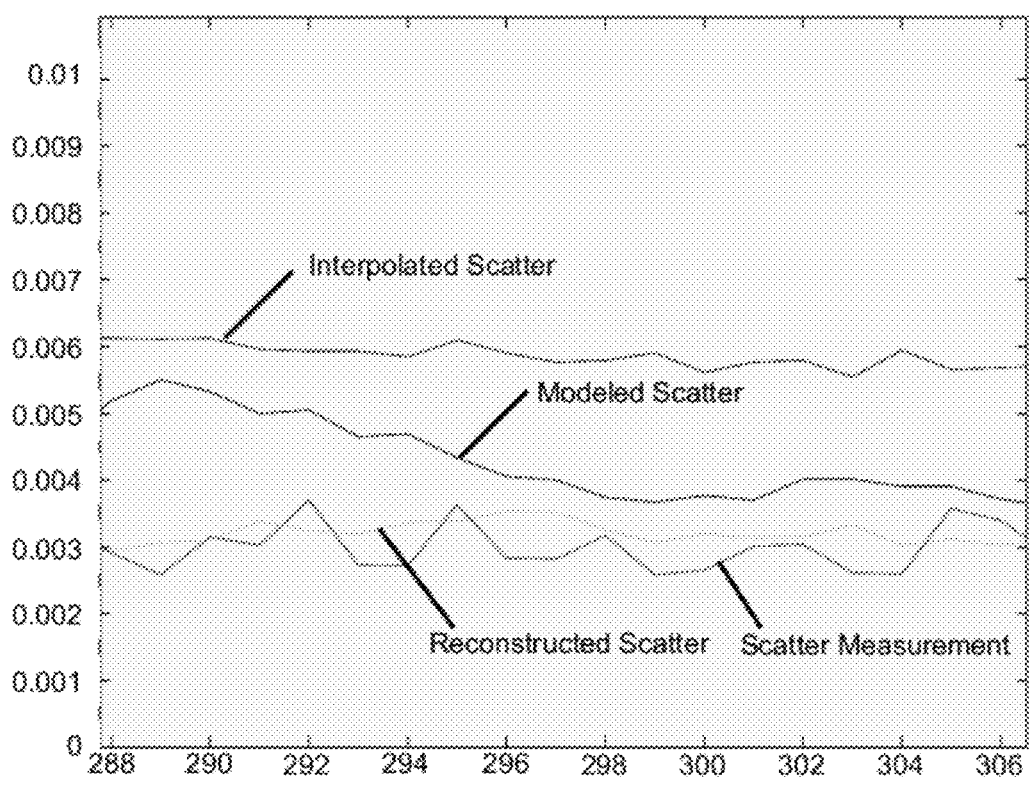

FIGS. 19a-19c show the 1-D profiles of the scatter map for the first projection (FIG. 19a) with an interpolation method, a modeled method and the current invention, together with the benchmark, the measured scatter signal. FIG. 19c shows the zoom-in picture of those results for central range of [288 306]. The current invention outperforms others in this region (the shadow behind the phantom), whose importance is more than the shadow of air.

Literatures also support the second assumption, and various scatter models have been built based on their own estimations. The defects for those methods are that the proposed models is restricted the scatter from only one single machine and its own setups. Different from those methods, which try to directly fit the scatter estimation into a certain model. The current embodiment of the invention only uses the scatter estimation from the current model as a constraint of the scatter distribution.

Generally, projection data consists of primary signal and scatter signal, and the latter can be express as the convolution of primary with a kernel function as $$I = I_{primary} + I_{scatter}$$
$$= I_{primary} + k(u, v) \otimes I_{primary}.$$

where I, $I_{primary}$ and $I_{scatter}$ denotes the total influence, the primary signal and the scatter signal, respectively. k(u,v) is the convolution kernel for the estimation of scatter signal from the primary. Anisotropic kernels have been demonstrated to be more effective than isotropic ones, and the freedom of nonlinearity is also given to the kernel. In this description, given the task to estimate the scatter in ROR with only boundary information, a simple nonlinear, projection based anisotropic kernel is provided for regulating the scatter distribution in ROR area:

$$I'_{scatter} \approx a \cdot I^b,$$

where $I_{scatter}$ is the bilinear interpolated scatter from the boundary scatters. a and b are undetermined model coefficients which show the overall magnitude adjustment and local adjustment based on the projections, respectively. Since one aspect of this embodiment is only to approximate the scatter distribution, it can be relaxed to give the lower and upper bound of the scatter distribution. The approximate regulation of $$I'_{scatter} \approx a \cdot I^b,$$

is formulated as a constraint:

$$\|I_{scatter} - \tilde{I}_{scatter}\|_1 = \|I_{scatter} - a \cdot I^b\|_1 < \epsilon \cdot I,$$

where $\epsilon \cdot I$ is a function of the projection I which controls the fidelity of the true scatter with the model data. The choice of $\epsilon$ should be within a proper range, since too tight constraint won't fit the nonlinear model to each pixel and too loose constraint will reduce the efficacy of this model. Therefore, $\epsilon$ is manually set to be 0.3 in this work. $\tilde{I}_{scatter}$ represents the pre-computed scatter from our model. Since the constraint in $$\|I_{scatter} - \tilde{I}_{scatter}\|_1 = \|I_{scatter} - a \cdot I^b\|_1 < \epsilon \cdot I,$$

is pixel-wised, it is equivalent to the following form:

$$\|I_{scatter,(i,j)} - \tilde{I}_{scatter,(i,j)}\|_1 < \epsilon \cdot I_{i,j},$$

where $I'_{scatter,(I,j)}$, $\tilde{I}_{scatter(i,j)}$, $I_{i,j}$ represent the scatter variable, pre-computed scatter and projection at pixel (i,j), respectively.

Different from algorithms aiming to reconstruct a scatter free image, the scatter correction algorithm focus on reconstructing a complete scatter distribution for each projection, namely scatter maps. The assumptions lead us to try to reconstruct the scatter maps via the constraint optimization (CO) with the recent developed and powerful tool of compressed sensing (CS) technique. For each projection, the detailed scatter correction involves the following steps:

(1) The boundary scatter map is extracted from each projection data and those scatter profiles are used to determine the scatter for ROR.
(2) Bilinear interpolation of the boundary scatter data provides initial estimation of the scatter in ROR.
(3) Least square minimization is used to find the coefficients a and b in $I'_{scatter} \approx a \cdot I^b$, with $I'_{scatter}$ to be the bilinear interpolation result. And then those coefficients are used to calculate $\tilde{I}_{scatter}$ in $$\|I_{scatter} - \tilde{I}_{scatter}\|_1 = \|I_{scatter} - a \cdot I^b\|_1 < \epsilon \cdot I,$$

Note that the log transform of $I'_{scatter} \approx a \cdot I^b$, is employed to form affine function of $I'_{scatter}$ and $I$:

$$\log(I'_{scatter}) \approx \log(a) + b \log(I).$$

(4) A CO with CS technique is formulated based on the assumptions, and it is solved by using conjugate gradient method.

(5) Estimated scatter is subtracted from the original projection data with soft-threshold method, and FDK algorithm is used to reconstruct the scatter free image.

Turning now to compressed sensing optimization, when the blocked region is only at the boundary region, the scatter information in ROR is completely missing. However, the transformed scatter signal is proved to be sparse in the DCT domain. Recent development of the compressed sensing theory has demonstrated that sparse signal or signal which is sparse in certain domain can be accurately reconstructed from highly under sampled measurements via the L-1 norm minimization of the relative transformed signal. Several algorithms based on the compressed sensing theory have been proposed for CT image reconstruction and treatment planning. In this description, the scatter map reconstruction for each projection is formulated as a constraint optimization problem under the framework of compressed sensing theory:

$$\text{minimize} \|DCT2(x)\|_{l_1} = \|DCT1_{column}(DCT1_{row}(x))\|_{l_1} = \|A_1 A_2 x\|_{l_1} = \|Ax\|_{l_1}$$

$$\|x - \tilde{I}_{scatter}\|_1 \leq \epsilon \cdot I$$

$$x \geq 0$$

subject to $$x_{boundary} = I_{boundary},$$

where x is the desired scatter map and its size is the same as the projection size. DCT2 is the 2-D discrete cosine transform operator and it can be implemented equivalently by successive 1-D DCT operations column-wisely and row-wisely. $A_1$ and $A_2$ represent the equivalent matrix of the two 1-D DCT operations respectively, and $A = A_1 A_2$ is the equivalent 2-D DCT matrix. The first constraint corresponds to the projection based model in $$\|I_{scatter} - \tilde{I}_{scatter}\|_1 = \|I_{scatter} - a \cdot I^b\|_1 \leq \epsilon \cdot I,$$

and $\tilde{I}_{scatter}$ is pre-computed using least square minimization as in $$\|I_{scatter,(i,j)} - \tilde{I}_{scatter,(i,j)}\|_1 \leq \epsilon \cdot I_{i,j},$$

The second constraint is the positivity constraint of the scatter map. Data fidelity constraint is incorporated in the last constraint, where the collected boundary scatter $I_{boundary}$ is replicated to the optimizer. It can also be written as $F \cdot x = I_{boundary}$, where F is the sampling matrix of x.

Solving the constraint optimization above is challenging because the size of the variable x is usually too big for many solvers. For instance, the detector size of Varian STX True-Beam (Varian Medical System, Inc., Palo Alto) machine is 1024×768, and hence there are nearly 0.8 million variables. However, the DCT operation can be carried out very fast like Fast FT, hence, a conjugate gradient (CG) and back-tracking line search are used to solve this problem.

The detail of the solver is described here.

The CO in $\log(I'_{scatter}) \approx \log(a) + b\log(I)$ can be rewritten as:

Minimize $\|Ax\|_{l_1}$ $$\|x - \tilde{I}_{scatter}\|_1 \leq \epsilon \cdot I$$

subject to $$x \geq 0$$

$$F \cdot x = I_{boundary}.$$

Consider the following form of the unconstrained problem:

minimize $$f(x) = \|Ax\|_{l_1} + \lambda_1 \|Fx - I_{boundary}\|_2^2 + \lambda_2(-x)_+ + \lambda_3((x - \tilde{I}_{scatter} - \epsilon \cdot I)_+ + (-x + \tilde{I}_{scatter} - \epsilon \cdot I)_+),$$

where $\lambda_1$, $\lambda_3$ and $\lambda_3$ are the regularization parameters that determines the trade-off between each term. The first term is original objective function, promoting the sparsity of the signal in DCT domain. The second term is the data fidelity term, which requires the consistency of the reconstructed data with the sample measurements. The third term corresponds to positivity of the scatter signal, and the intuition is that negative part of the variable will be charged. The last term is for the scatter model constraint, and it regulates the variable within the estimated range by charging wherever it violates the constraints. If $\lambda_1$, $\lambda_3$ and $\lambda_3$ are properly chosen, solving the unconstrained problem in $$f(x) = \|Ax\|_{l_1} + \lambda_1 \|Fx - I_{boundary}\|_2^2 + \lambda_2(-x)_+ + \lambda_3((x - \tilde{I}_{scatter} - \epsilon \cdot I)_+ + (-x + \tilde{I}_{scatter} - \epsilon \cdot I)_+),$$

is equivalent to the constrained problem in $$\|x - \tilde{I}_{scatter}\|_1 \leq \epsilon \cdot I$$

$$x \geq 0$$

$$F \cdot x = I_{boundary}.$$

The current embodiment includes the nonlinear conjugate gradient method with back-tracking line search to solve the unconstrained problem where $f(x)$ is the cost function as in $$f(x) = \|Ax\|_{l_1} + \lambda_1 \|Fx - I_{boundary}\|_2^2 + \lambda_2(-x)_+ + \lambda_3((x - \tilde{I}_{scatter} - \epsilon \cdot I)_+ + (-x + \tilde{I}_{scatter} - \epsilon \cdot I)_+),$$

The gradient of $f(x)$ can be calculated as:

$$\nabla f(x) = \nabla \|Ax\|_{l_1} + 2\lambda_1 F^T(Fx - I_{boundary}) + \lambda_2(x<0) + \lambda_3((x > \tilde{I}_{scatter} - \epsilon \cdot I) + (x < \tilde{I}_{scatter} - \epsilon \cdot I))$$

where $\nabla$ is the gradient operator. The third term (x<0), having binary values with entry to be one if x<0 and zero if x≥0, is the gradient of (−x). The fourth term is in the similar form as for the gradient of the last term in $$\nabla f(x) = \nabla \|Ax\|_{l_1} + 2\lambda_1 F^T(Fx - I_{boundary}) + \lambda_2(x<0) + \lambda_3((x > \tilde{I}_{scatter} - \epsilon \cdot I) + (x < \tilde{I}_{scatter} - \epsilon \cdot I))$$

The L-1 norm in here is the sum of absolute values for all entries, and hence it is not a smooth function. Instead, we approximate the L-1 norm function by using $\|x\| \approx \sqrt{x \cdot x + u}$, where u is a small positive smoothing parameter. In this exemplary embodiment, u is chosen to be $10^{-10}$. With this approximation, $$\frac{d|x|}{x} \approx \frac{x}{\sqrt{x \cdot x + u}}.$$

By using this approximation, the gradient of the $\|Ax\|_{l_1}$ can be expressed as:

$$\nabla \|Ax\|_{l_1} = A^T \Sigma^{-1} Ax,$$

where $\Sigma$ is a diagonal matrix with the diagonal elements $\Sigma_{ii} = \sqrt{(A_x)_i^T (A_x)_i + u}$. Therefore, the gradient for the objective function can be written as:

$$\nabla f(x) = A^T \Sigma^{-1} Ax + 2\lambda_1 F^T(Fx - I_{boundary}) + \lambda_2(x<0) + \lambda_3 (x > \tilde{I}_{scatter} - \epsilon \cdot I) + (x < \tilde{I}_{scatter} - \epsilon \cdot I))$$

Note that matrix A is the DCT operator, so it can be carried out very fast. The rest of the computation for the gradient only involves some relatively easy operations, so the overall gradient can be implemented very fast.

The time consuming part in the CG is the backtracking line search, because approximations were used for the unconstrained problem. The number of CG iterations varies with different choice of parameters, problem size and accuracy. In this exemplary embodiment, around 30 CG iterations will produce the satisfying result.

Turning now to evaluation, the current embodiment is evaluated with Varian STX TrueBeam. This machine is the cutting-edge in radiation therapy. A standard protocol was used in clinic was used in experiments. The x-ray tube operated at 100 kVp and 138 mA with the pulse width at each projection angle of 11 ms. Data of a 360° scan includes about 656 projections with an angle interval of about 0.54°. Each acquired projection image contains 1024×768 pixels with pixel size to be 0.388×0.388 mm. The source-to-axis distance (SAD) was 1000 mm and the source-to-imager distance (SID) was 1500 mm.

Two types of lead sheets are used in experiments: stripped lead sheets and boundary lead sheets. The first type was used to test the relation of the distance of the gap and the accuracy of the reconstructed scatter map. The spacing of the strips was made even distributed, but the boundaries of the strips were determined by the signal strength in the projections for exact accuracy. The second type was to demonstrate the scatter correction result and a predetermined distance of the gap in projection space. Both lead sheets are mounted to the outside surface of the collimator with the predetermined distance of about to the x-ray focal spot. The lead strips had an appropriate thickness for x-ray attenuation. For the stripped lead sheet, comparisons of the reconstructed scatter map with the measured signal are provided with increased distance of gaps to illustrate the performance of the proposed method. For the boundary lead sheet, comparisons of scatter corrected reconstruction image with the uncorrected reconstructed image are presented. In the quantitative analysis, reconstruction values are in the window of [0 1] and then compared with the measured signal. The relative reconstructed error (RRE) is calculated as:

$$RRE = \sqrt{\text{mean}\left[\left(\frac{u_i - \bar{u}_i}{\bar{u}_i}\right)^2\right]}$$

where $u_i$ is the reconstructed scatter map and $\bar{u}_i$ is the corresponding acquired scatter profile as the benchmark.

Regarding the results of the exemplary experiment for the current embodiment. As the distance of the gap between two boundary blockers is increased, the RRE can be summarized into Table II. If the table is viewed row-wise, within the same gap distance, the current embodiment always has smaller RRE compared with the measured scatter. The performance of the interpolation method and the modeling method is undetermined. If this table is viewed column-wise, with the gap of blockers narrowing, the RREs for both interpolation method and modeling method monotonically decrease, while the RRE for the current embodiment decreases until the last test. In general, with smaller distance, the modeling method will provide better result.

TABLE II

Gap distance and RRE for the head phantom

| Gap Distance (# of pixels) | Distance (mm) | Interpolation RRE | Model RRE | Proposed Method RRE |
|---|---|---|---|---|
| 618 | 239.7840 | 0.9801 | 1.4462 | 0.9118 |
| 452 | 175.3760 | 0.7423 | 0.6269 | 0.3366 |
| 292 | 113.2960 | 0.6888 | 0.5154 | 0.2759 |
| 130 | 50.4400 | 0.5140 | 0.4793 | 0.3433 |

Figure 20:
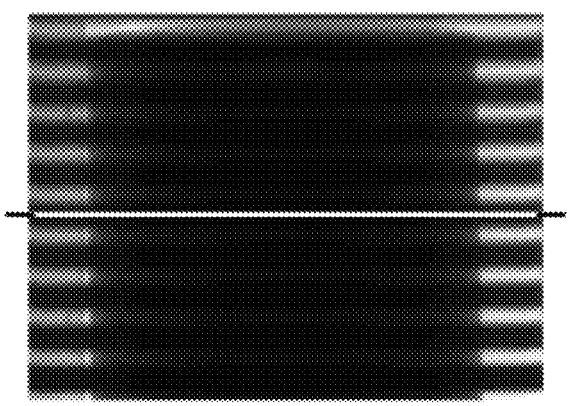
FIGS. 20a-20b show the scatter reconstruction results with interpolation method, modeling method, one embodiment of the invention and the benchmark.
Figure 20:
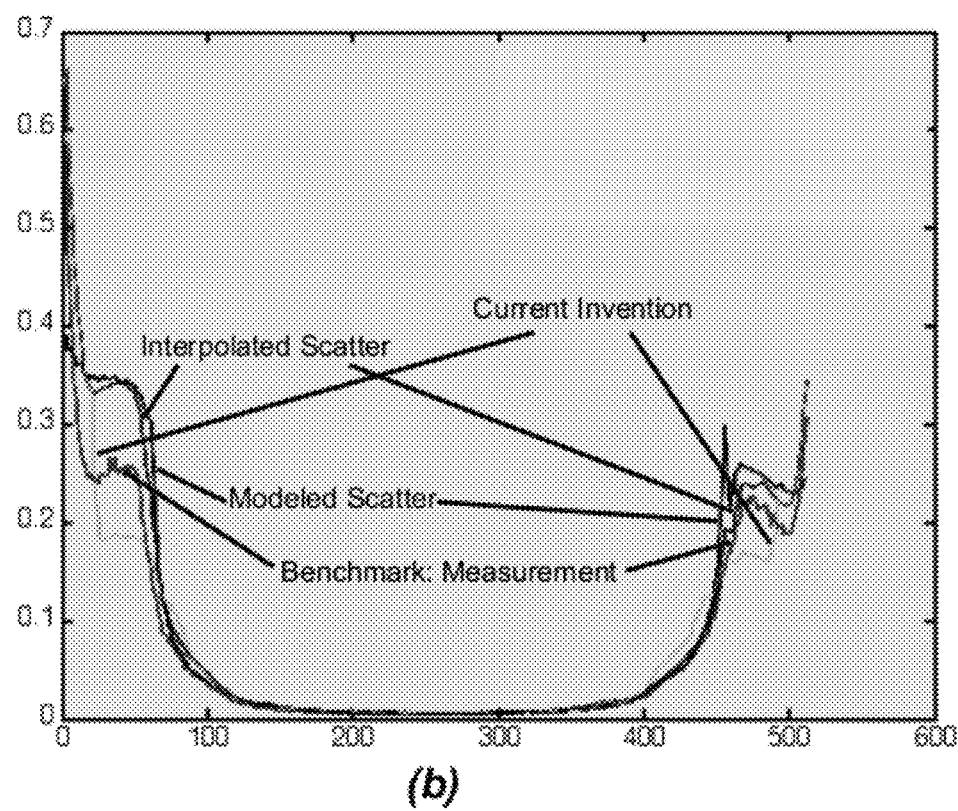

Turning now to the Catphan phantom, FIGS. 20a-20b show the scatter reconstruction results with interpolation method, modeling method, proposed method and the benchmark. Due to the high conformity of the Catphan phantom, the scatter behind the shadow of the object is nearly constant. Therefore, the performances of the interpolation method and the current embodiment tend to be similar. With the distance and RRE experiment (Table III), it can be found that the interpolation method outperforms the current embodiment when the gap distance is below 452 pixels, though the improvement is only in a very limited range (around 10%). As the distance reaches the largest 614 pixels, current embodiment demonstrates very stable performance as small gap distance (actually the performance is even better in this case), while RRE of the interpolation method increased about two-folded compared to the average value for small distance.

TABLE III

Gap distance and RRE for the Catphan phantom

| Gap Distance (# of pixels) | Distance (mm) | Interpolation RRE | Model RRE | Proposed Method RRE |
|---|---|---|---|---|
| 614 | 238.2320 | 0.6527 | 0.3725 | 0.2082 |
| 452 | 175.3760 | 0.2408 | 0.2323 | 0.2938 |
| 290 | 112.5200 | 0.2348 | 0.2633 | 0.2737 |
| 130 | 50.4400 | 0.1744 | 0.2229 | 0.2346 |

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art.

All such variations are considered to be within the scope and spirit of the present invention as defined by the following claims and their legal equivalents.

What is claimed:

1. A method of correcting scatter-induced artifacts in cone-beam computed tomography (CBCT), comprising:
   a. disposing blockers between an imaging source and a patient and disposing said patient between said blocker and a detector, wherein said detector comprises a region of reconstruction (ROR), wherein said blockers block the boundaries of said ROR;
   b. acquiring CBCT projection data on said ROR while rotating said imaging source, said blocker and said detector about an axis of said patient, wherein said projection data comprises primary signal data and scatter signal data, wherein said scatter signal data comprises a convolution of said primary signal data with a kernel function, wherein said convolution kernel function estimates said scatter signal data from said primary signal data; and
   c. correcting said CBCT projection data for said scatter signal data in said ROR comprising:

i. extracting a boundary scatter map from said ROR;

ii. initially estimating said boundary scatter signal data in said ROR using interpolation of said boundary scatter data;

iii. determining an overall magnitude adjustment and a local adjustment of said bilinear interpolated scatter using a least squares minimization;

iv. estimating a scatter map by reconstructing a complete scatter distribution for each said projection using a constraint optimization (CO) and a compressed sensing (CS);

v. subtracting said scatter map from said projection signal data; and vi. using a half-fan or full-fan tomographic reconstruction algorithm wherein said half-fan or full-fan tomographic reconstruction algorithm comprises a Feldkamp-Davis-Kress (FDK) algorithm or regularized iterative reconstruction algorithm, to reconstruct a scatter free image.

2. The method according to claim 1, wherein said projection image acquisition comprises using asymmetric half beam blockers.

3. The method according to claim 1, wherein said total variation regularization algorithm comprises a total variation regularized Feldkamp-Davis-Kress (FDK) algorithm based on a cosine weighting function.

4. The method according to claim 1, wherein said variation regularization algorithm is applied according to a minimization using a steepest gradient decent optimization method.

5. The method according to claim 1, wherein said scatter and image data are obtained simultaneously.

6. The method according to claim 1, wherein said projection image comprises using a half beam blocker, wherein said half beam blocker comprises unblocked regions on a first half side of a projection region and partially blocked regions on a second half side of said projection region.

7. The method according to claim 1, wherein said corrected scatter-induced artifacts in said projection image are accomplished from a single-rotation CBCT scan.

8. The method according to claim 1, wherein said interpolation and/or extrapolation of said projection image comprises a 1D cubic B-Spline interpolation/extrapolation applied to said projection imaged, where patient specific scatter information is derived by using scatter distributions on blocker strips.

9. The method according to claim 1, wherein said blocker comprises lead.

10. The method according to claim 1, wherein said blockers are arranged in a pattern, wherein said pattern of blockers is selected from the group consisting of horizontal strips, vertical strips, diagonal strips, checker board, asymmetric horizontal strips, and asymmetric vertical strips.

11. The method according to claim 1, wherein said blockers are moved actively during said projection image acquisition, wherein said blocker motion is selected from the group consisting of moving blockers relative to a stationary target, a moving target relative to stationary blockers, said moving blockers and said moving target, and rotating said target about a target axis, wherein said target axis is parallel to an axis of symmetry of said target pattern.

12. The method according to claim 1, wherein said blockers are arranged in a pattern, wherein said pattern of blockers are arranged according to a thickness of each said blocker.

13. The method according to claim 1, wherein said blockers are moved actively during said projection image acquisition, wherein said blocker motion comprises moving a focal point of said radiation source relative to said blocker position or moving a position of said radiation source relative to said blocker position.

14. The method according to claim 1, wherein said scatter data is acquired at an acquisition frequency that is lower that an acquisition frequency of said image data.

15. A method of correcting scatter-induced artifacts in transmission computed tomography (CT), comprising:

a. acquiring a CT projection image, wherein said projection image comprises unblocked regions and partially blocked regions, wherein said blocking comprises using beam blockers;

b. estimating a scatter map in said projection image by interpolation and/or extrapolation of said projection image and a corresponding opposing conjugate projection, wherein said corresponding opposing conjugated projection comprises a projection after an approximately 180 degree rotation of a radiation source and an attached partial blocker about an imaging subject;

c. subtracting said estimated scatter map from said projection image to obtain scatter-corrected projections;

d. using an appropriately programmed computer to operate a half-fan or full-fan tomographic reconstruction algorithm to reconstruct a scatter free image, wherein said tomographic reconstruction algorithm comprises an analytical Feldkamp-Davis-Kress (FDK) algorithm or regularized iterative reconstruction algorithm;

e. optionally, applying an iterative regularization process to suppress the noise level on said reconstructed CT volume, wherein scatter-induced artifacts are corrected; and f. applying a variation regularization algorithm according to a minimization using a steepest gradient decent optimization method.

16. The method according to claim 15, wherein said projection image acquisition comprises using asymmetric half beam blockers.

17. The method according to claim 15, wherein said total variation regularization algorithm comprises a total variation regularized Feldkamp-Davis-Kress (FDK) algorithm based on a cosine weighting function.

18. The method according to claim 15, wherein said scatter and image data are obtained simultaneously.

19. The method according to claim 15, wherein said projection image comprises using a half beam blocker, wherein said half beam blocker comprises unblocked regions on a first half side of a projection region and partially blocked regions on a second half side of said projection region.

20. The method according to claim 15, wherein said corrected scatter-induced artifacts in said projection image are accomplished from a single-rotation CBCT scan.

21. The method according to claim 15, wherein said interpolation and/or extrapolation of said projection image comprises a 1D cubic B-Spline interpolation/extrapolation applied to said projection imaged, where patient specific scatter information is derived by using scatter distributions on blocker strips.

22. The method according to claim 15, wherein said blocker comprises lead.

23. The method according to claim 15, wherein said blockers are arranged in a pattern, wherein said pattern of blockers is selected from the group consisting of horizontal strips, vertical strips, diagonal strips, checker board, asymmetric horizontal strips, and asymmetric vertical strips.

24. The method according to claim 15, wherein said blockers are moved actively during said projection image acquisition, wherein said blocker motion is selected from the group consisting of moving blockers relative to a stationary target, a moving target relative to stationary blockers, said moving blockers and said moving target, and rotating said target about a target axis, wherein said target axis is parallel to an axis of symmetry of said target pattern.

25. The method according to claim 15, wherein said blockers are arranged in a pattern, wherein said pattern of blockers are arranged according to a thickness of each said blocker.

26. The method according to claim 15, wherein said blockers are moved actively during said projection image acquisition, wherein said blocker motion comprises moving a focal point of said radiation source relative to said blocker position or moving a position of said radiation source relative to said blocker position.

27. The method according to claim 15, wherein said scatter data is acquired at an acquisition frequency that is lower that an acquisition frequency of said image data.

* * * * *